US011274321B2

(12) United States Patent
Reed et al.

(10) Patent No.: US 11,274,321 B2
(45) Date of Patent: Mar. 15, 2022

(54) USE OF OXYHYDROGEN MICROORGANISMS FOR NON-PHOTOSYNTHETIC CARBON CAPTURE AND CONVERSION OF INORGANIC AND/OR C1 CARBON SOURCES INTO USEFUL ORGANIC COMPOUNDS

(71) Applicant: Kiverdi, Inc., Hayward, CA (US)

(72) Inventors: John S. Reed, Hayward, CA (US); Lisa Dyson, Hayward, CA (US)

(73) Assignee: Kiverdi, Inc., Pleasanton, CA (US)

( * ) Notice: Subject to any disclaimer, the term of this patent is extended or adjusted under 35 U.S.C. 154(b) by 0 days.

(21) Appl. No.: 15/963,536

(22) Filed: Apr. 26, 2018

(65) Prior Publication Data
US 2018/0245108 A1   Aug. 30, 2018

Related U.S. Application Data

(63) Continuation of application No. 13/643,872, filed as application No. PCT/US2011/034218 on Apr. 27, (Continued)

(51) Int. Cl.
   *C12N 1/20*   (2006.01)
   *C12P 7/62*   (2006.01)
   (Continued)

(52) U.S. Cl.
   CPC ............. *C12P 7/625* (2013.01); *C12M 23/34* (2013.01); *C12M 29/02* (2013.01); *C12M 29/08* (2013.01);
   (Continued)

(58) Field of Classification Search
   CPC .... C12P 7/00; C12P 1/04; C12P 7/625; C12P 7/6463; C12M 29/06; C12M 29/00;
   (Continued)

(56) References Cited

U.S. PATENT DOCUMENTS

| 4,426,450 A * | 1/1984 | Donofrio | C12M 29/06 |
| | | | 435/243 |
| 2009/0130706 A1* | 5/2009 | Berzin | C12M 21/02 |
| | | | 435/41 |
| 2012/0015413 A1* | 1/2012 | Sichwart | C12N 1/20 |
| | | | 435/134 |

OTHER PUBLICATIONS

Volova et al., Appl Microbiol Biotechnol, 58:675-678, 2002 (Year: 2002).*

(Continued)

*Primary Examiner* — Allison M Fox
*Assistant Examiner* — Qing Xu
(74) *Attorney, Agent, or Firm* — FisherBroyles, LLP; Jill A. Jacobson

(57) ABSTRACT

Compositions and methods for a hybrid biological and chemical process that captures and converts carbon dioxide and/or other forms of inorganic carbon and/or CI carbon sources including but not limited to carbon monoxide, methane, methanol, formate, or formic acid, and/or mixtures containing CI chemicals including but not limited to various syngas compositions, into organic chemicals including biofuels or other valuable biomass, chemical, industrial, or pharmaceutical products are provided. The present invention, in certain embodiments, fixes inorganic carbon or CI carbon sources into longer carbon chain organic chemicals by utilizing microorganisms capable of performing the oxyhydrogen reaction and the autotrophic fixation of $CO_2$ in one or more steps of the process.

38 Claims, 5 Drawing Sheets

Related U.S. Application Data 2011, which is a continuation-in-part of application No. PCT/US2010/001402, filed on May 12, 2010, which is a continuation-in-part of application No. 12/613,550, filed on Nov. 6, 2009, now abandoned.

(60) Provisional application No. 61/111,794, filed on Nov. 6, 2008.

(51) Int. Cl.

| | | |
|---|---|---|
| *C12P 7/625* | (2022.01) | |
| *C12M 1/00* | (2006.01) | |
| *C12N 1/12* | (2006.01) | |
| *C25B 15/02* | (2021.01) | |
| *C12P 7/6463* | (2022.01) | |
| *C25B 1/04* | (2021.01) | |

(52) U.S. Cl.
CPC ............ *C12M 29/18* (2013.01); *C12M 29/20* (2013.01); *C12M 43/04* (2013.01); *C12M 47/02* (2013.01); *C12N 1/12* (2013.01); *C12N 1/20* (2013.01); *C12N 1/205* (2021.05); *C12P 7/6463* (2013.01); *C25B 1/04* (2013.01); *C25B 15/02* (2013.01); *Y02E 60/36* (2013.01); *Y02P 20/133* (2015.11)

(58) Field of Classification Search
CPC .......... C12M 47/02; C12N 1/20; C12N 1/205; C25B 1/04; Y02P 20/133; Y02P 20/582
See application file for complete search history.

(56) References Cited

OTHER PUBLICATIONS

Schlegel et al., In: Advances in Biochemical Engineering, 1971, vol. 1, pp. 143-168. (Year: 1971).*

DeCicco, B.T., Removal of Eutrophic Nutrients from Wastewater and their Bioconversion to Bacterial Single Cell Protein for Animal Feed Supplements Phase 1, Water Resources Research Center, Washington Technical Institute, Washington, D.C. 20008, Nov. 1977.

DeCicco, B.T., Eutrophic Nutrients from Wastewater and their Bioconversion to Bacterial Single Cell Protein for Animal Feed Supplements Phase II, Water Resources Research Center, University of the District of Columbia, Van Ness Campus, Washington, D.C. 20008, Apr. 1979.

U.S. Appl. No. 16/013,833, Office Action, dated Apr. 18, 2019.

* cited by examiner

USE OF OXYHYDROGEN MICROORGANISMS FOR NON-PHOTOSYNTHETIC CARBON CAPTURE AND CONVERSION OF INORGANIC AND/OR C1 CARBON SOURCES INTO USEFUL ORGANIC COMPOUNDS

RELATED APPLICATIONS

This application is a continuation of U.S. application Ser. No. 13/643,872, filed Mar. 1, 2013, which is a national stage of International Patent Application No. PCT/US2011/034218, filed Apr. 27, 2011, which claims priority under 35 U.S.C. § 119(e) to U.S. Provisional Patent Application No. 61/328,184, filed Apr. 27, 2010 and entitled "USE OF OXYHYDROGEN MICROORGANISMS FOR NON-PHOTOSYNTHETIC CARBON CAPTURE AND CONVERSION OF INORGANIC CARBON SOURCES INTO USEFUL ORGANIC COMPOUNDS." International Patent Application No. PCT/US2011/034218 is also a continuation-in-part of International Patent Application No. PCT/US2010/001402, filed May 12, 2010, and entitled "BIOLOGICAL AND CHEMICAL PROCESS UTILIZING CHEMOAUTOTROPHIC MICROORGANISMS FOR THE CHEMOSYNTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS," which is a continuation-in-part of U.S. patent application Ser. No. 12/613,550, filed Nov. 6, 2009, and entitled "BIOLOGICAL AND CHEMICAL PROCESS UTILIZING CHEMOAUTOTROPHIC MICROORGANISMS FOR THE CHEMOSYNTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS," which claims the benefit of U.S. Provisional Patent Application No. 61/111,794, filed Nov. 6, 2008, and entitled, "BIOLOGICAL AND CHEMICAL PROCESS UTILIZING CHEMOAUTOTROPHIC MICROORGANISMS FOR THE RECYCLING OF CARBON FROM CARBON DIOXIDE AND OTHER INORGANIC CARBON SOURCES THROUGH CHEMOSYNTHESIS INTO BIOFUEL AND ADDITIONAL USEFUL PRODUCTS." Each of these applications is incorporated herein by reference in its entirety for all purposes.

FIELD OF INVENTION

The present invention falls within the technical areas of biofuels, bioremediation, carbon capture, carbon dioxide-to-fuels, carbon recycling, carbon sequestration, energy storage, gas-to-liquids, waste energy to fuels, syngas conversions, and renewable/alternative and/or low carbon dioxide emission sources of energy. Specifically the present invention is a unique example of the use of biocatalysts within a biological and chemical process to fix carbon dioxide and/or other forms of inorganic carbon and/or or other C1 carbon sources into longer carbon chain organic chemical products in a non-photosynthetic process powered by low carbon emission energy sources and/or waste energy sources. In addition the present invention involves the production of chemical co-products that are co-generated through carbon-fixation reaction steps and/or non-biological reaction steps as part of an overall carbon capture and conversion process or syngas conversion process. The present invention can enable the effective and economic capture of carbon dioxide from the atmosphere or from a point source of carbon dioxide emissions as well as the economic use of waste energy sources and/or renewable energy sources and/or low carbon emission energy sources, for the production of liquid transportation fuel and/or other organic chemical products, which will help address greenhouse gas induced climate change and contribute to the domestic production of renewable liquid transportation fuels and/or other organic chemicals without any dependence upon agriculture.

BACKGROUND

Great interest and resources have been directed towards developing technologies that use renewable energy or waste energy for the conversion of carbon dioxide, or other low value carbon sources, into useful organic chemicals in order to provide alternatives to chemicals, materials and fuels derived from petroleum or other fossil sources. Most of the focus in the area of $CO_2$ conversion has been placed on biological approaches that utilize photosynthesis to fix $CO_2$ into biomass or end-products, while some effort has been directed at fully abiotic and chemical processes for fixing $CO_2$.

A type of $CO_2$-to-organic chemical approach that has received relatively less attention is hybrid chemical/biological processes where the biological step is limited to $CO_2$ fixation alone, corresponding to the dark reaction of photosynthesis. The potential advantages of such a hybrid $CO_2$-to-organic chemical process include the ability to combine enzymatic capabilities gained through billions of years of evolution in fixing $CO_2$, with a wide array of abiotic technologies to power the process such as solar PV, solar thermal, wind, geothermal, hydroelectric, or nuclear. Microorganisms performing carbon fixation without light can be contained in more controlled and protected environments, less prone to water and nutrient loss, contamination, or weather damage, than what can be used for culturing photosynthetic microorganisms. Furthermore an increase in bioreactor capacity can be met with vertical rather than horizontal construction, making it potentially far more land efficient. A hybrid chemical/biological system offers the possibility of a $CO_2$-to-organic chemical process that avoids many drawbacks of photosynthesis while retaining the biological capabilities for complex organic synthesis from $CO_2$.

Chemoautotrophic microorganisms are generally microbes that can perform $CO_2$ fixation like in the photosynthetic dark reaction, but which can get the reducing equivalents needed for $CO_2$ fixation from an inorganic external source, rather than having to internally generate them through the photosynthetic light reaction. Carbon fixing biochemical pathways that occur in chemoautotrophs include the reductive tricarboxylic acid cycle, the Calvin-Benson-Bassham cycle, and the Wood-Ljungdahl pathway.

Prior work is known relating to certain applications of chemoautotrophic microorganisms in the capture and conversion of $CO_2$ gas to fixed carbon. However, many of these approaches have suffered shortcomings that have limited the effectiveness, economic feasibility, practicality and commercial adoption of the described processes. The present invention in certain aspects addresses one or more of the aforementioned shortcomings.

It is believed that the present invention utilizing oxyhydrogen microorganisms in the chemosynthetic fixation of $CO_2$ under carefully controlled oxygen levels may have advantages for the production of longer chain organic compounds (e.g., $C_5$ and longer). The ability to produce longer chain organic compounds is an important advantage for the present invention since the energy densities (energy per unit volume) are generally higher for longer chain organic compounds, and the compatibility with the current transportation fleet is generally greater relative to, for example, shorter chain products such as C1 and C2 products.

SUMMARY OF THE INVENTION

In response to a need in the art that the inventors have recognized in making the invention, a novel combined biological and chemical process for the capture and conversion of inorganic carbon and/or C1 carbon sources to longer chain organic compounds, and particularly organic compounds with C5 or longer chain lengths, through the use of oxyhydrogen microorganisms for carbon capture and fixation is described. In some embodiments, the process can couple the efficient production of high value organic compounds such as liquid hydrocarbon fuel with the disposal of waste sources of carbon, as well as with the capture of $CO_2$, which can generate additional revenue.

In one aspect, a biological and chemical method for the capture and conversion of an inorganic carbon compound and/or an organic compound containing only one carbon atom into an organic chemical product is described. In some embodiments, the method comprises introducing an inorganic carbon compound and/or an organic compound containing only one carbon atom into an environment suitable for maintaining oxyhydrogen microorganisms and/or capable of maintaining extracts of oxyhydrogen microorganisms; and converting the inorganic carbon compound and/or the organic compound containing only one carbon atom into the organic chemical product and/or a precursor thereof within the environment via at least one chemosynthetic carbon-fixing reaction utilizing the oxyhydrogen microorganisms and/or cell extracts containing enzymes from the oxyhydrogen microorganisms. In some embodiments, the chemosynthetic fixing reaction is at least partially driven by chemical and/or electrochemical energy provided by electron donors and electron acceptors that have been generated chemically and/or electrochemically and/or are introduced into the environment from at least one source external to the environment.

In one aspect, a bioreactor is described. The bioreactor comprises, in one set of embodiments, a first column comprising an upper portion and a lower portion; and a second column comprising an upper portion and a lower portion, the upper portion of the second column fluidically connected to the upper portion of the first column, and the lower portion of the second column fluidically connected to the lower portion of the first column. In some embodiments, the bioreactor is constructed and arranged such that, when a liquid is circulated between the first and second columns, a volume of gas is substantially stationary at the top of the first column and/or the second column. In some embodiments, the volume of gas occupies at least about 2% of the total volume of the column in which the volume is positioned.

In another aspect, a method of operating a bioreactor is provided. The method comprises, in some embodiments, circulating a liquid comprising a growth medium between a first column and a second column, wherein, during operation, a volume of gas remains substantially stationary at the top of the first column and/or the second column, and the volume of gas occupies at least about 2% of the total volume of the column in which the volume is positioned.

In one aspect, an electrolysis device is provided. In some embodiments, the electrolysis device comprises a chamber constructed and arranged to electrolyze water to produce oxygen and hydrogen; and an outlet comprising a separator constructed and arranged to separate at least a portion of the oxygen within a stream from at least a portion of the hydrogen within a stream such that the hydrogen content of the fluid exiting the separator is suitable for use as a feed stream to a reactor containing a culture of oxyhydrogen microorganisms.

In another aspect, a method of operating an electrolysis device is described. The method comprises, in some embodiments, electrolyzing water to produce a first stream containing oxygen and hydrogen; and separating at least a portion of the oxygen from at least a portion of the hydrogen to produce a second stream relatively rich in hydrogen compared to the first stream, wherein the second stream is suitable for use as a feed stream to a reactor containing a culture of oxyhydrogen microorganisms.

The present invention, in certain embodiments, provides compositions and methods for the capture of carbon dioxide from carbon dioxide-containing gas streams and/or atmospheric carbon dioxide or carbon dioxide in dissolved, liquefied or chemically-bound form through a chemical and biological process that utilizes obligate or facultative oxyhydrogen microorganisms, and/or cell extracts containing enzymes from oxyhydrogen microorganisms in one or more carbon fixing process steps.

The present invention, in certain embodiments, provides compositions and methods for the utilization of C1 carbon sources including but not limited to carbon monoxide, methane, methanol, formate, or formic acid, and/or mixtures containing C1 chemicals including but not limited to various syngas compositions generated from various gasified, pyrolyzed, or steam-reformed fixed carbon feedstocks, and convert said C1 chemicals into longer chain organic compounds, The present invention, in certain embodiments, provides compositions and methods for the recovery, processing, and use of the organic compounds produced by chemosynthetic reactions performed by oxyhydrogen microorganisms to fix inorganic carbon and/or C1 carbon sources into longer chain organic compounds. The present invention, in certain embodiments, provides compositions and methods for the maintenance and control of the oxygen levels in the carbon-fixation environment for the enhanced (e.g., optimal) production of C5 or longer organic compound products through carbon fixation. The present invention, in certain embodiments, provides compositions and methods for the generation, processing and delivery of chemical nutrients needed for carbon-fixation and maintenance of oxyhydrogen microorganism cultures, including but not limited to the provision of electron donors and electron acceptors needed for non-photosynthetic carbon-fixation. The present invention, in certain embodiments, provides compositions and methods for the maintenance of an environment conducive for carbon-fixation, and the recovery and recycling of unused chemical nutrients and process water.

The present invention, in certain embodiments, provides compositions and methods for chemical process steps that occur in series and/or in parallel with the chemosynthetic reaction steps that: convert unrefined raw input chemicals to more refined chemicals that are suited for supporting the chemosynthetic carbon fixing step; that convert energy inputs into a chemical form that can be used to drive chemosynthesis, and specifically into chemical energy in the form of electron donors and electron acceptors; that direct inorganic carbon captured from industrial or atmospheric or aquatic sources to the carbon fixation steps of the process under conditions that are suitable to support chemosynthetic carbon fixation by the oxyhydrogen microorganisms or enzymes and/or direct C1 chemicals derived from low value or waste sources of carbon such as carbon monoxide, methane, methanol, formate, or formic acid, and/or mixtures containing C1 chemicals including but not limited to various syngas compositions derived from the gasification, pyrolysis, or steam reforming of various low value or waste carbon sources, that can be used by the oxyhydrogen microorganism as a carbon sources and any energy source for the synthesis of longer chain organic chemicals; that further process the output products of the carbon fixation steps into a form suitable for storage, shipping, and sale, and/or safe disposal in a manner that results in a net reduction of gaseous $CO_2$ released into the atmosphere and/or the upgrade of a low value or waste material into a finished chemical, fuel, or nutritional product. The fully chemical process steps combined with the chemosynthetic carbon fixation steps constitute the overall carbon capture and conversion process of some embodiments of the present invention.

One feature of certain embodiments of the present invention is the inclusion of one or more process steps within a chemical process for the capture of inorganic carbon and conversion to fixed carbon products, that utilize oxyhydrogen microorganisms and/or enzymes from oxyhydrogen microorganisms as a biocatalyst for the fixation of carbon dioxide in carbon dioxide-containing gas streams or the atmosphere or water and/or dissolved or solid forms of inorganic carbon, into organic compounds. In some such embodiments carbon dioxide containing flue gas, or process gas, or air, or inorganic carbon in solution as dissolved carbon dioxide, carbonate ion, or bicarbonate ion including aqueous solutions such as sea water, or inorganic carbon in solid phases such as but not limited to carbonates and bicarbonates, is pumped or otherwise added to a vessel or enclosure containing nutrient media and oxyhydrogen microorganisms. In some such cases oxyhydrogen microorganisms perform chemosynthesis to fix inorganic carbon into organic compounds using the chemical energy stored in molecular hydrogen and/or valence or conduction electrons in solid state electrode materials and/or one or more of the following list of electron donors pumped or otherwise provided to the nutrient media including but not limited to: ammonia; ammonium; carbon monoxide; dithionite; elemental sulfur; hydrocarbons; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite; transition metals or their sulfides, oxides, chalcogenides, halides, hydroxides, oxyhydroxides, phosphates, sulfates, or carbonates, in soluble or solid phases. In some embodiments, conduction or valence band electrons in solid state electrode materials can be used. The electron donors can be oxidized by electron acceptors in the chemosynthetic reaction. Electron acceptors that may be used at the chemosynthetic reaction step include oxygen and/or other electron acceptors including but not limited to one or more of the following: carbon dioxide, ferric iron or other transition metal ions, nitrates, nitrites, sulfates, oxygen, or valence or conduction band holes in solid state electrode materials.

One feature of certain embodiments of the present invention is the inclusion of one or more process steps within a chemical process for the conversion of C1 carbon sources including but not limited to carbon monoxide, methane, methanol, formate, or formic acid, and/or mixtures containing C1 chemicals including but not limited to various syngas compositions generated from various gasified, pyrolyzed, or steam-reformed fixed carbon feedstocks, that utilize oxyhydrogen microorganisms and/or enzymes from oxyhydrogen microorganisms as a biocatalyst for the conversion of C1 chemicals into longer chain organic chemicals (i.e. C2 or longer and, in some embodiments, C5 or longer carbon chain molecules). In some such embodiments C1 containing syngas, or process gas, or C1 chemicals in a pure liquid form or dissolved in solution is pumped or otherwise added to a vessel or enclosure containing nutrient media and oxyhydrogen microorganisms. In some such cases oxyhydrogen microorganisms perform biochemical synthesis to elongate C1 chemicals into longer carbon chain organic chemicals using the chemical energy stored in the C1 chemical, and/or molecular hydrogen and/or valence or conduction electrons in solid state electrode materials and/or one or more of the following list of electron donors pumped or otherwise provided to the nutrient media including but not limited to: ammonia; ammonium; carbon monoxide; dithionite; elemental sulfur; hydrocarbons; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite; transition metals or their sulfides, oxides, chalcogenides, halides, hydroxides, oxyhydroxides, sulfates, or carbonates, in soluble or solid phases. The electron donors can be oxidized by electron acceptors in a chemosynthetic reaction. Electron acceptors that may be used at this reaction step include oxygen and/or other electron acceptors including but not limited to one or more of the following: carbon dioxide, ferric iron or other transition metal ions, nitrates, nitrites, oxygen, or holes in solid state electrode materials.

The chemosynthetic reaction step or steps of the process whereby carbon dioxide and/or inorganic carbon is fixed into organic carbon in the form of organic compounds and biomass and/or the reaction steps converting C1 chemicals to longer chain organic chemicals whereby a C1 chemical such as but not limited to carbon monoxide, methane, methanol, formate, or formic acid, and/or mixtures containing C1 chemicals including but not limited to various syngas compositions generated from various gasified, pyrolyzed, or steam-reformed fixed carbon feedstocks, are biochemically converted into longer chain organic chemicals (i.e. C2 or longer and, in some embodiments, C5 or longer carbon chain molecules) can be performed in aerobic, microaerobic, anoxic, anaerobic conditions, or facultative conditions. A facultative environment is considered to be one having aerobic upper layers and anaerobic lower layers caused by stratification of the water column.

The oxygen level is controlled in some embodiments of the current invention so that the production of targeted organic compounds by the oxyhydrogen microorganisms through carbon-fixation is controlled (e.g., optimized). One objective of controlling oxygen levels is to control (e.g., optimize) the intracellular Adenosine Triphosphate (ATP) concentration through the cellular reduction of oxygen and production of ATP by oxidative phosphorylation, while simultaneously keeping the environment sufficiently reducing so that a high ratio of NADH (or NADPH) to NAD (or NADP) is also maintained.

An advantage of using oxyhydrogen microorganisms over strictly anaerobic acetogenic or methanogenic microorganisms for carbon capture applications and/or syngas conversion applications is the higher oxygen tolerance of oxyhydrogen microorganisms.

A further advantage of using oxyhydrogen microorganisms for carbon capture applications and/or syngas conversion applications and/or biofuel production over using acetogens is that the production of ATP powered by the oxyhydrogen reaction results in a water product, which can readily be incorporated into the process stream, rather than the generally undesirable acetic acid or butyric acid products of acidogenesis which can harm the microorganisms by dropping the solution pH or accumulating to toxic levels.

An additional feature of certain embodiments of the present invention regards the source, production, or recycling of the electron donors used by the oxyhydrogen microorganisms to fix carbon dioxide into organic compounds and/or to synthesize longer carbon chain organic molecules from C1 chemicals. The electron donors used for carbon dioxide capture and carbon fixation can be produced or recycled in certain embodiments of the present invention electrochemically or thermochemically using power from a number of different renewable and/or low carbon emission energy technologies including but not limited to: photovoltaics, solar thermal, wind power, hydroelectric, nuclear, geothermal, enhanced geothermal, ocean thermal, ocean wave power, tidal power. The electron donors can also be of mineralogical origin including but not limited to reduced S and Fe containing minerals. The electron donors used in certain embodiments of the present invention can also be produced or recycled through chemical reactions with hydrocarbons that may or may not be a non-renewable fossil fuel, but where said chemical reactions produce low or zero carbon dioxide gas emissions. For example oxide reduction reactions that produce a carbonate and a hydrogen product that can be used as electron donor in the carbon-fixation reaction steps of certain embodiments of the present invention include:

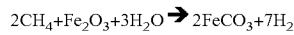

$$2CH_4 + Fe_2O_3 + 3H_2O \rightarrow 2FeCO_3 + 7H_2$$

and/or

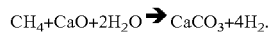

$$CH_4 + CaO + 2H_2O \rightarrow CaCO_3 + 4H_2.$$

An additional feature of certain embodiments of the present invention regards the formation and recovery of organic compounds and/or biomass from the chemosynthetic carbon fixation step or steps. These organic compounds and/or biomass products can have a variety of applications.

An additional feature of certain embodiments of the present invention regards using modified oxyhydrogen microorganisms in the carbon-fixation step/steps such that a superior quantity and/or quality of organic compounds, biochemicals, or biomass is generated through chemosynthesis. The oxyhydrogen microbes used in these steps may be modified through artificial means including but not limited to accelerated mutagenesis (e.g. using ultraviolet light or chemical treatments), genetic engineering or modification, hybridization, synthetic biology or traditional selective breeding. Possible modifications of the oxyhydrogen microorganisms include but are not limited to those directed at producing increased quantity and/or quality of organic compounds and/or biomass to be used as a biofuels, or as feedstock for the production of biofuels including, but not limited to JP-8 jet fuel, diesel, gasoline, biodiesel, butanol, ethanol, hydrocarbons, methane, and pseudovegetable oil or any other hydrocarbon suitable for use as a renewable/alternate fuel leading to lowered greenhouse gas emissions.

Also described are compositions and methods that reduce the hazards of performing gas fermentations that utilize mixtures of hydrogen and oxygen within the invented process.

Compositions and methods that take advantage of the oxygen tolerance and ability to use oxygen as an electron acceptor possessed by oxyhydrogen microorganisms in order to enable a system for converting water into hydrogen or hydride electron donors and oxygen electron acceptors, that has improved efficiency over the application of current state-of-the-art electrolysis for the purpose of generating hydrogen or hydride electron donors and oxygen electron acceptors, are also described.

Also described are process steps for the recovery and further finishing of useful chemicals produced both by the biological carbon fixation steps of the process, as well as from non-biological process steps.

Other advantages and novel features of the present invention will become apparent from the following detailed description of various non-limiting embodiments of the invention when considered in conjunction with the accompanying figures. All publications, patent applications and patents mentioned in the text are incorporated by reference in their entirety. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
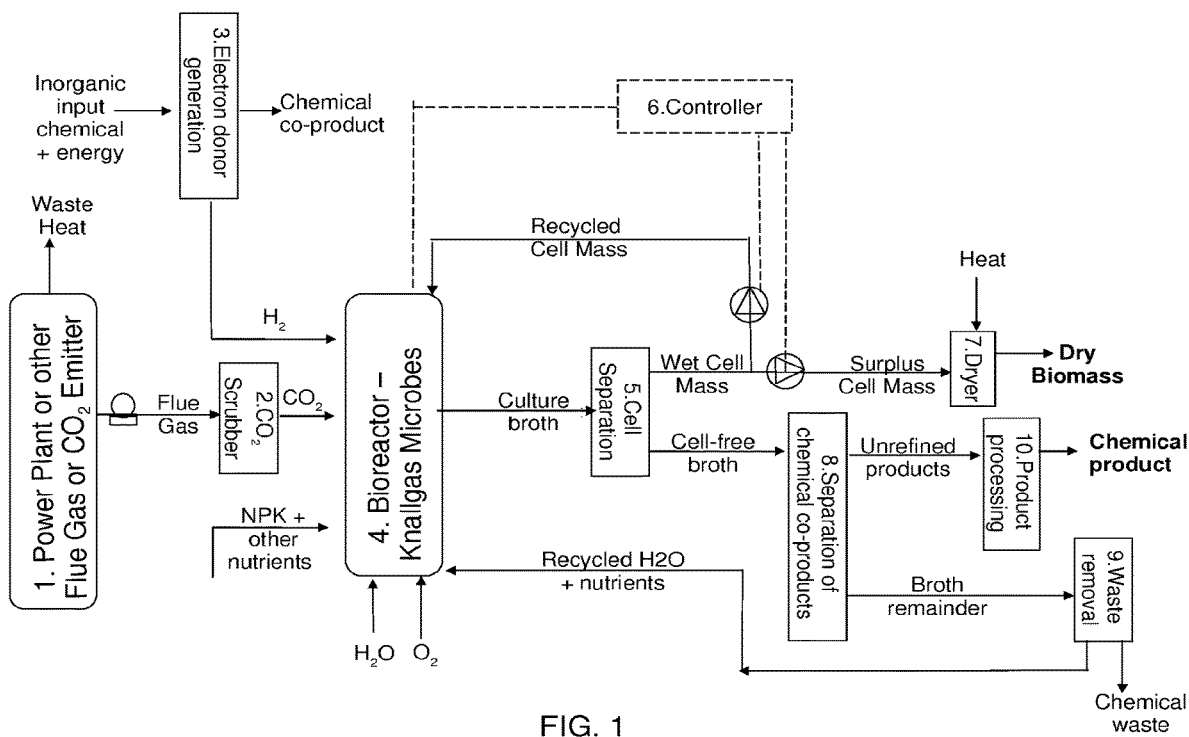
FIG. 1 is a general process flow diagram for one embodiment of this invention for a carbon capture and fixation process.

The present invention provides, in certain embodiments, compositions and methods for the capture and fixation of carbon dioxide from carbon dioxide-containing gas streams and/or atmospheric carbon dioxide or carbon dioxide in liquefied or chemically-bound form through a chemical and biological process that utilizes obligate or facultative oxyhydrogen microorganisms, and/or cell extracts containing enzymes from oxyhydrogen microorganisms in one or more process steps. The fixation of inorganic carbon sources other than $CO_2$ and/or other C1 carbon sources are also described. Cell extracts include but are not limited to: a lysate, extract, fraction or purified product exhibiting chemosynthetic enzyme activity that can be created by standard methods from oxyhydrogen microorganisms. In addition the present invention, in certain embodiments, provides compositions and methods for the recovery, processing, and use of the chemical products of chemosynthetic reaction step or steps performed by oxyhydrogen microorganisms to fix inorganic carbon into organic compounds and/or synthetic reaction step or steps performed by oxyhydrogen microorganisms to elongate C1 molecules to longer carbon chain organic chemicals. Finally the present invention, in certain embodiments, provides compositions and methods for the production and processing and delivery of chemical nutrients needed for chemoautotrophic carbon-fixation by the oxyhydrogen microorganisms, and particularly electron donors including but not limited to molecular hydrogen and/or electrical power, and electron acceptors including but not limited to oxygen and carbon dioxide to drive the carbon fixation reaction; compositions and methods for the maintenance of an environment conducive for carbon-fixation by oxyhydrogen microorganisms; and compositions and methods for the removal of the chemical products of chemosynthesis from the oxyhydrogen culture environment and the recovery and recycling of unused of chemical nutrients.

The terms "molecular hydrogen," "dihydrogen," and "$H_2$" are used interchangeably throughout.

The terms "oxyhydrogen microorganism" and "knallgas microorganism" are used interchangeably throughout. Oxyhydrogen microorganisms are generally described in Chapter 5, Section III of *Thermophilic Bacteria*, a book by Jakob Kristjansson, CRC Press, 1992, which is incorporated herein by reference. Generally, oxyhydrogen microorganisms are capable of performing the oxyhydrogen reaction. Oxyhydrogen microorganisms generally have the ability to use molecular hydrogen by means of hydrogenases with some of the electrons donated from $H_2$ being utilized for the reduction of $NAD^+$ (and/or other intracellular reducing equivalents) and the rest of the electrons for aerobic respiration. In addition, oxyhydrogen microorganisms generally are capable of fixing $CO_2$ autotrophically, through pathways such as the reverse Calvin Cycle or the reverse citric acid cycle.

In addition, the terms "oxyhydrogen reaction" and "knallgas reaction" are used interchangeably throughout to refer to the microbial oxidation of molecular hydrogen by molecular oxygen. The oxyhydrogen reaction is generally expressed as:

and/or by stoichiometric equivalents of this reaction.

Exemplary oxyhydrogen microorganisms that can be used in one or more process steps of certain embodiments of the present invention include but are not limited to one or more of the following: purple non-sulfur photosynthetic bacteria including but not limited to *Rhodopseudomonas palustris*, *Rhodopseudomonas capsulata*, *Rhodopseudomonas viridis*, *Rhodopseudomonas sulfoviridis*, *Rhodopseudomonas blastica*, *Rhodopseudomonas spheroides*, *Rhodopseudomonas acidophila* and other *Rhodopseudomonas* sp., *Rhodospirillum rubrum*, and other *Rhodospirillum* sp.; *Rhodococcus opacus* and other *Rhodococcus* sp.; *Rhizobium japonicum* and other *Rhizobium* sp.; *Thiocapsa roseopersicina* and other *Thiocapsa* sp.; *Pseudomonas hydrogenovora*, *Pseudomonas hydrogenothermophila*, and other *Pseudomonas* sp.; *Hydrogenomonas pantotropha*, *Hydrogenomonas eutropha*, *Hydrogenomonas facilis*, and other *Hydrogenomonas* sp.; *Hydrogenobacter thermophilus* and other *Hydrogenobacter* sp.; *Hydrogenovibrio marinus* and other *Hydrogenovibrio* sp.; *Helicobacter pylori* and other *Helicobacter* sp.; *Xanthobacter* sp.; *Hydrogenophaga* sp.; *Bradyrhizobium japonicum* and other *Bradyrhizobium* sp.; *Ralstonia eutropha* and other *Ralstonia* sp.; *Alcaligenes eutrophus* and other *Alcaligenes* sp.; *Variovorax paradoxus*, and other *Variovorax* sp.; *Acidovorax facilis*, and other *Acidovorax* sp.; cyanobacteria including but not limited to *Anabaena oscillarioides*, *Anabaena spiroides*, *Anabaena cylindrica*, and other *Anabaena* sp.; green algae including but not limited to *Scenedesmus obliquus* and other *Scenedesmus* sp., *Chlamydomonas reinhardii* and other *Chlamydomonas* sp., *Ankistrodesmus* sp., *Rhaphidium polymorphium* and other *Rhaphidium* sp.; as well as a consortiums of microorganisms that include oxyhydrogen microorganisms.

The different oxyhydrogen microorganisms that can be used in certain embodiments of the present invention may be native to a range environments including but not limited to hydrothermal vents, geothermal vents, hot springs, cold seeps, underground aquifers, salt lakes, saline formations, mines, acid mine drainage, mine tailings, oil wells, refinery wastewater, oil, gas, or hydrocarbon contaminated waters; coal seams, the deep sub-surface, waste water and sewage treatment plants, geothermal power plants, sulfatara fields, soils including but not limited to soils contaminated with hydrocarbons and/or located under or around oil or gas wells, oil refineries, oil pipelines, gasoline service stations. They may or may not be extremophiles including but not limited to thermophiles, hyperthermophiles, acidophiles, halophiles, and psychrophiles.

In some embodiments, relatively long-chain chemical products can be produced. For example, the organic chemical product produced in some embodiments can include compounds with carbon chain lengths of at least C5, at least C10, at least C15, at least C20, between about C5 and about C30, between about C10 and about C30, between about C15 and about C30, or between about C20 and about C30.

FIG. 1 illustrates the general process flow diagram for embodiments of the present invention that have a process step for the generation of electron donors (e.g., molecular hydrogen electron donors) suitable for supporting chemosynthesis from an energy input and raw inorganic chemical input; followed by recovery of chemical co-products from the electron donor generation step; delivery of generated electron donors along with oxygen electron acceptors, water, nutrients, and $CO_2$ from a point industrial flue gas source, into chemosynthetic reaction step or steps that make use of oxyhydrogen microorganisms to capture and fix carbon dioxide, creating chemical and biomass co-products through chemosynthetic reactions; followed by process steps for the recovery of both chemical and biomass products from the process stream; and recycling of unused nutrients and process water, as well as cell mass needed to maintain the microbial culture, back into the carbon-fixation reaction steps.

In the embodiment illustrated in FIG. 1, the $CO_2$ containing flue gas is captured from a point source or emitter.

Electron donors (e.g., $H_2$) needed for chemosynthesis can be generated from input inorganic chemicals and energy. The flue gas can be pumped through bioreactors containing oxyhydrogen microorganisms along with electron donors and acceptors needed to drive chemosynthesis and a medium suitable to support the microbial culture and carbon fixation through chemosynthesis. The cell culture may be continuously flowed into and out of the bioreactors. After the cell culture leaves the bioreactors, the cell mass can be separated from the liquid medium. Cell mass needed to replenish the cell culture population at a desirable (e.g., optimal) level can be recycled back into the bioreactor. Surplus cell mass can be dried to form a dry biomass product which can be further post-processed into various chemical, fuel, or nutritional products. Following the cell separation step, extracellular chemical products of the chemosynthetic reaction can be removed from the process flow and recovered. Then, any undesirable waste products that might be present are removed. Following this, the liquid medium and any unused nutrients can be recycled back into the bioreactors.

Many of the reduced inorganic chemicals upon which chemoautotrophs grow (e.g. $H_2$, $H_2S$, ferrous iron, ammonium, $Mn^{2+}$) can be readily produced using electrochemical and/or thermochemical processes known in the art of chemical engineering that may optionally be powered by a variety carbon dioxide emission-free or low-carbon emission and/or renewable sources of power including wind, hydroelectric, nuclear, photovoltaics, or solar thermal.

Certain embodiments of the present invention use carbon dioxide emission-free or low-carbon emission and/or renewable sources of power in the production of electron donors including but not limited to one or more of the following: photovoltaics, solar thermal, wind power, hydroelectric, nuclear, geothermal, enhanced geothermal, ocean thermal, ocean wave power, tidal power. In certain embodiments of the present invention oxyhydrogen microorganisms function as biocatalysts for the conversion of renewable energy and/or low or zero carbon emission energy into liquid hydrocarbon fuel, or high energy density organic compounds generally, with $CO_2$ captured from flue gases, or from the atmosphere, or ocean serving as a carbon source. These embodiments of the present invention can provide renewable energy technologies with the capability of producing a transportation fuel having significantly higher energy density than if the renewable energy sources are used to produce hydrogen gas—which must be stored in relatively heavy storage systems (e.g. tanks or storage materials)—or if it is used to charge batteries, which have relatively low energy density. Additionally the liquid hydrocarbon fuel product of certain embodiments of the present invention may be more compatible with the current transportation infrastructure compared to battery or hydrogen energy storage options.

The position of the process step or steps for the generation of electron donors (e.g., molecular hydrogen electron donors) in the general process flow of certain embodiments of the present invention is illustrated in FIG. 1 by Box 3, labeled "Electron Donor Generation." Electron donors produced in certain embodiments of the present invention using electrochemical and/or thermochemical processes known in the art of chemical engineering and/or generated from natural sources include, but are not limited to molecular hydrogen and/or valence or conduction electrons in solid state electrode materials and/or other reducing agents including but not limited to one or more of the following: ammonia; ammonium; carbon monoxide; dithionite; elemental sulfur; hydrocarbons; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite; transition metals or their sulfides, oxides, chalcogenides, halides, hydroxides, oxyhydroxides, sulfates, or carbonates, in soluble or solid phases.

Certain embodiments of the present invention use molecular hydrogen as the electron donor. Hydrogen electron donors are generated by methods known in to art of chemical and process engineering including but not limited to one or more of the following: through electrolysis of water by approaches including but not limited to using Proton Exchange Membranes (PEM), liquid electrolytes such as KOH, high-pressure electrolysis, high temperature electrolysis of steam (HTES); thermochemical splitting of water through methods including but not limited to the iron oxide cycle, cerium(IV) oxide-cerium(III) oxide cycle, zinc zinc-oxide cycle, sulfur-iodine cycle, copper-chlorine cycle, calcium-bromine-iron cycle, hybrid sulfur cycle; electrolysis of hydrogen sulfide; thermochemical and/or electrochemical splitting of hydrogen sulfide; other electrochemical or thermochemical processes known to produce hydrogen with low- or no-carbon dioxide emissions including but not limited to: carbon capture and sequestration enabled methane reforming; carbon capture and sequestration enabled coal gasification; the Kværner-process and other processes generating a carbon-black product; carbon capture and sequestration enabled gasification or pyrolysis of biomass; and the half-cell reduction of $H^+$ to $H_2$ accompanied by the half-cell oxidization of electron sources including but not limited to ferrous iron ($Fe^{2+}$) oxidized to ferric iron ($Fe^{3+}$) or the oxidation of sulfur compounds whereby the oxidized iron or sulfur can be recycled to back to a reduced state through additional chemical reaction with minerals including but not limited to metal sulfides, hydrogen sulfide, or hydrocarbons.

In certain embodiment of the present invention, hydrogen electron donors are not necessarily generated with low- or no-carbon dioxide emissions, however the hydrogen is generated from waste or low value sources of energy using methods known in to art of chemical and process engineering including but not limited to gasification, pyrolysis, or steam-reforming of feedstock such as but not limited to municipal waste, black liquor, agricultural waste, wood waste, stranded natural gas, biogas, sour gas, methane hydrates, tires, sewage, manure, straw, and low value, highly lignocellulosic biomass in general.

In certain embodiments of the present invention that utilize molecular hydrogen as an electron donor for the carbon-fixation reactions performed by oxyhydrogen microorganisms, there can be a chemical co-product formed in the generation of molecular hydrogen using a renewable and/or $CO_2$ emission-free energy input. If water is used as a hydrogen source, then oxygen can be a co-product of water splitting through processes including but not limited to electrolysis or thermochemical water splitting. In certain embodiments of the present invention using water as a hydrogen source, some of the oxygen co-product can be used in the oxyhydrogen carbon fixation step for the production of intracellular ATP through the oxyhydrogen reaction enzymatically linked to oxidative phosphorylation. In certain embodiments of the present invention, the oxygen produced by water-splitting in excess of what is required to maintain favorable (e.g., optimal) conditions for carbon fixation and organic compound production by the oxyhydrogen microorganisms can be processed into a form suitable for sale through process steps known in the art and science of commercial oxygen gas production. In certain embodiments of the present invention where hydrogen sulfide is the hydrogen source, sulfur or sulfuric acid can be a chemical co-product of molecular hydrogen production. In certain embodiments of the present invention where sulfuric acid is a co-product of hydrogen production, some of the sulfuric acid can be used in the hydrolysis of biomass in post-carbon fixation process steps. In certain embodiments of the present invention, excess sulfuric acid and/or sulfur that is co-produced (e.g., beyond what can be used elsewhere in the carbon capture and conversion process of certain embodiments of the present invention) can be processed into a form suitable for sale through process steps known in the art and science of commercial sulfuric acid and/or sulfur production. Process heat can also be generated in the production of hydrogen from hydrogen sulfide. In certain embodiments of the present invention, process heat generated in hydrogen production is recovered and utilized elsewhere in the carbon capture and conversion process of certain embodiments of the present invention to improve overall energy efficiency. A chemical and/or heat and/or electrical co-product can accompany the generation of molecular hydrogen for use as an electron donor in certain embodiments of the present invention. The chemical and/or heat and/or electrical co-products of molecular hydrogen generation can be used to the extent possible elsewhere in the carbon capture and conversion process of certain embodiments of the present invention, for example, in order to improve efficiency In certain embodiments, additional chemical co-product (e.g., beyond what can be used in the carbon capture and conversion process of certain embodiments of the present invention) can be prepared for sale in order to generate an additional stream of revenue. Excess heat or electrical energy co-product in the production of molecular hydrogen (e.g., beyond what can be used internally in the process) can be delivered for sale, for example, for use in another chemical and/or biological process through means known in the art and science heat exchange and transfer and electrical generation and transmission, including but not limited to the conversion of process heat to electrical power in a form that can be sold.

Certain embodiments of the present invention utilize electrochemical energy stored in solid-state valence or conduction electrons within an electrode or capacitor or related devices, alone or in combination with chemical electron donors and/or electron mediators to provide the oxyhydrogen microorganisms reducing equivalents for the carbon-fixation reactions by means of direct exposure of said electrode materials to the microbial culturing environment and/or immersion of said electrode materials within the microbial culture medium.

A feature of certain embodiments of the present invention regards the production, or recycling of electron donors generated from mineralogical origin that may also be used by certain oxyhydrogen microbes as a source of reducing equivalents in addition, or in lieu of hydrogen, including but not limited to electron donors generated from reduced S and Fe containing minerals. Hence the present invention, in certain embodiments, can enable the use of a largely untapped source of energy—inorganic geochemical energy.

The electron donors used in certain embodiments of the present invention may be refined from natural mineralogical sources which include but are not limited to one or more of the following: elemental $Fe^0$; siderite ($FeCO_3$); magnetite ($Fe_3O_4$); pyrite or marcasite ($FeS_2$), pyrrhotite ($Fe_{(1-x)}S$ ($x=0$ to 0.2)), pentlandite ($Fe,Ni)_9S_8$, violarite ($Ni_2FeS_4$), bravoite ($Ni,Fe)S_2$, arsenopyrite (FeAsS), or other iron sulfides; realgar (AsS); orpiment ($As_2S_3$); cobaltite (CoAsS); rhodochrosite ($MnCO_3$); chalcopyrite ($CuFeS_2$), bornite ($Cu_5FeS_4$), covellite (CuS), tetrahedrite ($Cu_8Sb_2S_7$), enargite ($Cu_3AsS_4$), tennantite ($Cu_{12}As_4 \cdot S_{13}$), chalcocite ($Cu_2S$), or other copper sulfides; sphalerite (ZnS), marmatite (ZnS), or other zinc sulfides; galena (PbS), geocronite ($Pb_5(Sb,As_2)S_8$), or other lead sulfides; argentite or acanthite ($Ag_2S$); molybdenite ($MoS_2$); millerite (NiS), polydymite ($Ni_3S_4$) or other nickel sulfides; antimonite ($Sb_2S_3$); $Ga_2S_3$; CuSe; cooperite (PtS); laurite ($RuS_2$); braggite (Pt,Pd,Ni)S; $FeCl_2$.

The generation of electron donor from natural mineralogical sources includes a preprocessing step in certain embodiments of the present invention which can include but is not limited to comminuting, crushing or grinding mineral ore to increase the surface area for leaching with equipment such as a ball mill and wetting the mineral ore to make a slurry. In these embodiments of the present invention where electron donors are generated from natural mineral sources, it may be advantageous if particle size is controlled so that the sulfide and/or other reducing agents present in the ore may be concentrated by methods known to the art including but not limited to: flotation methods such as dissolved air flotation or froth flotation using flotation columns or mechanical flotation cells; gravity separation; magnetic separation; heavy media separation; selective agglomeration; water separation; or fractional distillation. After the production of crushed ore or slurry, the particulate matter in the leachate or concentrate may be separated by filtering (e.g. vacuum filtering), settling, or other well known techniques of solid/liquid separation, prior to introducing the electron donor containing solution to the chemoautotrophic culture environment. In addition anything toxic to the chemoautotrophs that is leached from the mineral ore may be removed prior to exposing the chemoautotrophs to the leachate. The solid left after processing the mineral ore may be concentrated with a filter press, disposed of, retained for further processing, or sold depending upon the mineral ore used in the particular embodiment of the invention.

The electron donors in certain embodiments of the present invention may also be refined from pollutants or waste products including but not limited to one or more of the following: process gas; tail gas; enhanced oil recovery vent gas; biogas; acid mine drainage; landfill leachate; landfill gas; geothermal gas; geothermal sludge or brine; metal contaminants; gangue; tailings; sulfides; disulfides; mercaptans including but not limited to methyl and dimethyl mercaptan, ethyl mercaptan; carbonyl sulfide; carbon disulfide; alkanesulfonates; dialkyl sulfides; thiosulfate; thiofurans; thiocyanates; isothiocyanates; thioureas; thiols; thiophenols; thioethers; thiophene; dibenzothiophene; tetrathionate; dithionite; thionate; dialkyl disulfides; sulfones; sulfoxides; sulfolanes; sulfonic acid; dimethylsulfoniopropionate; sulfonic esters; hydrogen sulfide; sulfate esters; organic sulfur; sulfur dioxide and all other sour gases.

In addition to mineralogical sources, electron donors are produced or recycled in certain embodiments of the present invention through chemical reactions with hydrocarbons that may be of fossil origin, but which are used in chemical reactions producing low or zero carbon dioxide gas emissions. These reactions include thermochemical and electrochemical processes. Such chemical reactions that are used in these embodiments of the present invention include but are not limited to: the thermochemical reduction of sulfate reaction or TSR and the Muller-Kuhne reaction; methane reforming-like reactions utilizing metal oxides in place of water such as but not limited to iron oxide, calcium oxide, or magnesium oxide whereby the hydrocarbon is reacted to form solid carbonate with little or no emissions of carbon dioxide gas along with hydrogen electron donor product.

Examples of reactions between metal oxides and hydrocarbons to produce a hydrogen electron donor product and carbonates include but are not limited to:

$$2CH_4 + Fe_2O_3 + 3H_2O \rightarrow 2FeCO_3 + 7H_2$$

and/or $$CH_4 + CaO + 2H_2O \rightarrow CaCO_3 + 4H_2.$$

In certain embodiments, the generated electron donors are oxidized in the chemosynthetic reaction step or steps by electron acceptors that include but are not limited to carbon dioxide, oxygen and/or one or more of the following: ferric iron or other transition metal ions, nitrates, nitrites, sulfates, or valence or conduction band holes in solid state electrode materials.

The position of the chemosynthetic and/or oxyhydrogen reaction step or steps in the general process flow of certain embodiments of the present invention is illustrated in FIG. 1 by Box 4 labeled "Bioreactor—Knallgas Microbes."

At each step in the process where chemosynthetic and/or oxyhydrogen reactions occur one or more types of electron donor and one or more types of electron acceptor may be pumped or otherwise added to the reaction vessel as either a bolus addition, or periodically, or continuously to the nutrient medium containing oxyhydrogen microorganisms. The chemosynthetic reaction driven by the transfer of electrons from electron donor to electron acceptor can fix inorganic carbon dioxide into organic compounds and biomass.

In certain embodiments of the present invention electron mediators may be included in the nutrient medium to facilitate the delivery of reducing equivalents from electron donors to oxyhydrogen organisms in the presence of electron acceptors and inorganic carbon in order to kinetically enhance the chemosynthetic reaction step. This aspect of the present invention can be used to enhance the transfer of reducing electrons to the oxyhydrogen microbes from poorly soluble electron donors such as but not limited to $H_2$ gas or electrons in solid state electrode materials using electron mediators known in the art of electrical stimulation of microbial metabolism including but not limited to anthroquinone-2,6-disulfonate (AQDS), cobalt sepulchrate, cytochromes, formate, humic substances, iron, methyl-viologen, NAD+/NADH, neutral red (NR), phenazines, and quinones.

The delivery of reducing equivalents from electron donors to the oxyhydrogen microorganisms for the chemosynthetic reaction or reactions can be kinetically and/or thermodynamically enhanced in certain embodiments through means including but not limited to: the introduction of hydrogen storage materials into the microbial culture environment that can double as a solid support media for microbial growth—bringing absorbed or adsorbed hydrogen electron donors into close proximity with the hydrogen-oxidizing chemoautotrophs and/or the introduction of electrode materials (e.g., graphite, graphite felt, activated carbon, carbon nanofibers, conductive polymers, steel, iron, copper, titanium, lead, tin, palladium, platinum, platinum-coated titanium, other platinum coated metals, transition metals, transition metal alloys, transition metal sulfides, oxides, chalcogenides, halides, hydroxides, oxyhydroxides, phosphates, sulfates, and/or carbonates) that can double as a solid growth support media and a source of electron donors or acceptors directly into the chemoautotrophic culture environment—bringing solid state electrons into close proximity with the microbes. Some such embodiments of the present invention can be useful for transferring reducing equivalents from poorly soluble electron donors such as but not limited to $H_2$ gas or electrons in solid state electrode materials to the oxyhydrogen microorganisms.

The culture broth used in the chemosynthetic steps of certain embodiments of the present invention may be an aqueous solution containing suitable minerals, salts, vitamins, cofactors, buffers, and other components needed for microbial growth, known to those skilled in the art [Bailey and Ollis, Biochemical Engineering Fundamentals, 2nd ed; pp 383-384 and 620-622; McGraw-Hill: New York (1986)]. These nutrients can be chosen to maximize carbon-fixation and promote the carbon flow through enzymatic pathways leading to desired organic compounds. Alternative growth environments such as those used in the arts of solid state or non-aqueous fermentation may be used in certain embodiments. In certain embodiments that utilize an aqueous culture, broth, salt water, sea water and/or water from other natural bodies of water, or other non-potable sources of water may be used when tolerated by the oxyhydrogen microorganisms.

The biochemical pathways may be controlled and optimized in certain embodiments of the present invention for the production of chemical products (e.g., targeted organic compounds) and/or biomass by maintaining specific growth conditions (e.g., levels of nitrogen, oxygen, phosphorous, sulfur, trace micronutrients such as inorganic ions, and if present any regulatory molecules that might not generally be considered a nutrient or energy source). Depending upon the embodiment of the invention the broth may be maintained in aerobic, microaerobic, anoxic, anaerobic, or facultative conditions. A facultative environment is considered to be one having aerobic upper layers and anaerobic lower layers caused by stratification of the water column.

The oxygen level is controlled in certain embodiments of the invention. The oxygen level can be controlled, for example, to enhance the production of targeted organic compounds by the oxyhydrogen microorganisms through carbon-fixation. One objective of controlling oxygen levels, in certain embodiments, is to control (e.g., optimize) the intracellular Adenosine Triphosphate (ATP) concentration through the cellular reduction of oxygen and production of ATP by oxidative phosphorylation. In some such embodiments, it can be desirable, while controlling ATP concentration, to simultaneously keep the environment sufficiently reducing so that the intracellular ratio of NADH (or NADPH) to NAD (or NADP) remains relatively high. In some embodiments, ATP levels are increased and/or optimized within the oxyhydrogen microorganisms by means including but not limited to one or more of the following: the cellular reduction of oxygen and/or another electron acceptor of sufficient oxidation strength for ATP production through oxidative phosphorylation; the direct introduction of ATP into the culture medium; and/or the direct introduction of chemical analogues of ATP into the culture medium.

The reduction of oxygen by hydrogen in the oxyhydrogen reaction is generally enzymatically linked to the production of ATP through oxidative phosphorylation in oxyhydrogen microorganisms. The oxyhydrogen reaction can act as a proxy for the light reaction in photosynthesis in generating both NADPH and ATP. Generally, in oxyhydrogen microorganisms, hydrogenase catalyzes the reduction of NAD to NADH by hydrogen (or, alternatively, in some photosynthetic organisms that are capable of carrying out the oxyhydrogen reaction, a hydrogenase catalyzes the reduction of ferrodoxin by $H_2$, which in turn reduces NADP to NADPH) [Chen, Gibbs, Plant Physiol. (1992) 100, 1361-1365]. NADH and/or NADPH can then be used as reducing agents for anabolic reactions, or to generate ATP by reducing oxygen through oxidative phosphorylation [Bongers, J. Bacteriology, (October 1970) 145-151]. Therefore, in place of the following light dependent photosynthetic reaction:

$$2H_2O+2NADP^++2ADP+2Pi+light \rightarrow 2NADPH+2H^++2ATP+O_2$$

an oxyhydrogen reaction of $$1/2O_2+2NADP^++2ADP+2Pi+3H_2 \rightarrow 2NADPH+2H^++2ATP+2H_2O$$

can occur in dark conditions (e.g., in the substantial absence of visible electromagnetic radiation), with hydrogen acting in the place of photons given the production of 2ATP per $H_2$ consumed [Bongers, J. Bacteriology, (October 1970) 145-151].

The maintenance of high intracellular concentrations of ATP as well as NADH and/or NADPH is targeted in certain embodiments of the present invention to promote carbon fixation and drive anabolic pathways and/or solventogenic pathways that consume reducing equivalents and either consume ATP, and/or that lower the net ATP yield of chemosynthetic carbon-fixation. Such biochemical pathways include but are not limited to the following: fatty acid synthesis; mevalonate pathway and terpenoid synthesis; butanol pathway and 1-butanol synthesis; acetolactate/alpha-ketovalerate pathway and 2-butanol synthesis; and the ethanol pathway. A preferred oxygen level can be determined, in some embodiments of in the present invention: too low an oxygen level can reduce the intracellular ATP in oxyhydrogen microorganisms below a desired level, while too high an oxygen level can decrease the NADH (or NADPH) to NAD (or NADP) ratio below a desired level.

The application of the oxyhydrogen reaction for the production of ATP and NADH and/or NADPH used for carbon fixation and synthesis of organic compounds in certain embodiments of the present invention can provide advantages over alternative approaches using, for example, anaerobic biochemical pathways for carbon-fixation for such as Wood-Ljungdahl or methanogenic pathways. Carbon-fixation through the Wood-Ljungdahl or methanogenic pathways generally produces C1 or C2 organic compounds and it can be difficult to produce longer than C4 compounds through these pathways.

The Wood-Ljungdahl pathway can produce acetic acid, ethanol, butyric acid, and butanol in nature, but butyric acid and butanol are generally minor products of $H_2$ and $CO_2$ gas fermentation, and chain lengths longer than C4 do not typically arise [Lynd, Zeikus, J. of Bacteriology (1983) 1415-1423; Eichler, Schink, Archives of Microbiology (1984) 140, 147-152]. The acetogenic pathways to acetic acid and butyric acid produce net ATP, while the solventogenic pathways to ethanol and butanol do not [Papoutsakis, Biotechnology & Bioengineering (1984) 26, 174-187; Heise, Muller, Gottschalk, J. of Bacteriology (1989) 5473-5478; Lee, Park, Jang, Nielsen, Kim, Jung, Biotechnology & Bioengineering (2008) 101, 2, 209-228]. Since ATP is needed for cell maintenance a certain amount of relatively undesirable non-biofuel co-product (ie organic acids) from acetogens fixing carbon through the Wood-Ljungdahl pathway will generally be present which constitutes a waste of reducing equivalents and carbon.

The production of hydrocarbons with chain length longer than C4 is most commonly accomplished biologically through fatty acid biosynthesis [Fischer, Klein-Marcuschamer, Stephanolpoulos, Metabolic Engineering (2008) 10, 295-304]. Unlike the solventogenic pathways coming out of the Wood-Ljungdahl pathway, fatty acid synthesis involves net ATP consumption. For example the following gives the net reaction for synthesis of Palmitic acid (C16), in this example starting from Acetyl-CoA:

$$8Acetyl\text{-}CoA+7ATP+H_2O+14NADPH+14H^+ \rightarrow Palmitic\ acid+8CoA+14NADP^++7ADP+7Pi$$

One difficulty with using anaerobic pathways such as Methanogenesis or Wood-Ljungdahl for ATP production to drive fatty acid synthesis is the ATP produced per $H_2$ consumed is relatively low: one ATP per $4H_2$ for methane [Thauer, R. K., Kaster, A. K., Seedorf, H., Buckel, W. & Hedderich, R. Methanogenic archaea: ecologically relevant differences in energy conservation. Nat Rev Microbiol 6, 579-591, doi:nrmicro1931 [pii]] or acetic acid production and one ATP per $10H_2$ for butyric acid production [Papoutsakis, Biotechnology & Bioengineering (1984) 26, 174-187; Heise, Muller, Gottschalk, J. of Bacteriology (1989) 5473-5478; Lee, Park, Jang, Nielsen, Kim, Jung, Biotechnology & Bioengineering (2008) 101, 2, 209-228]. By contrast, for the oxyhydrogen reaction, hydrogenotrophic oxyhydrogen microorganisms can produce up to two ATP per $H_2$ consumed [Bongers, J. Bacteriology, (October 1970) 145-151]. In other words oxyhydrogen microorganisms can produce up to eight times more ATP per $H_2$ consumed than methanogenic or acetogenic microorganisms. Furthermore the path to ATP production through the oxyhydrogen reaction produces water which can readily be incorporated into the process stream rather than the relatively undesirable acetic acid or butyric acid products of acidogenesis that can upset the system pH and can rise to concentrations toxic to the organisms.

The highest energy density fuel that can be practically reached naturally through the Wood-Ljungdahl pathway with inorganic carbon input is generally ethanol at 30 MJ/kg, although butanol at 36.1 MJ/kg might be possible. Production of diesel fuels (46.2 MJ/kg) or JP-8 aviation fuel (43.15 MJ/kg) can generally be difficult and is generally less efficient utilizing anaerobic pathways such as Wood-Ljungdahl due to the increased amount of $H_2$ that needs to be consumed in strictly anaerobic pathways per ATP produced, which is needed for fatty acid synthesis. However these high density, infrastructure compatible liquid fuels can be readily produced through fatty synthesis pathways driven by ATP and NADH or NADPH generated by the oxyhydrogen reaction.

Biomass lipid content and lipid biosynthetic pathway efficiency are two factors that can affect the overall efficiency of certain embodiments of the present invention for converting $CO_2$ and other C1 compounds to longer chain compounds (e.g., infrastructure-compatible fuels). The biomass lipid content can determine the proportion of carbon and reducing equivalents directed towards the synthesis of fuel products, as opposed to other components of biomass. The lipid content can determine the amount of energy input from the reducing equivalents that can be captured in final fuel product. Likewise, the metabolic pathway efficiency can determine the amount of reducing equivalents that must be consumed in converting $CO_2$ and hydrogen to lipid along the lipid biosynthetic pathway. Many oxyhydrogen microorganisms include species rich in lipid content and containing efficient pathways from $H_2$ and $CO_2$ to lipid. Certain embodiments of the present invention use species with high lipid contents such as but not limited to *Rhodococcus opacus* which can have a lipid content of over 70% [Gouda, M. K., Omar, S. H., Chekroud, Z. A. & Nour Eldin, H. M. Bioremediation of kerosene I: A case study in liquid media. Chemosphere 69, 1807-1814, doi:S0045-6535(07)00738-2; Waltermann, M., Luftmann, H., Baumeister, D., Kalscheuer, R. & Steinbuchel, A. *Rhodococcus opacus* strain PD630 as a new source of high-value single-cell oil? Isolation and characterization of triacylglycerols and other storage lipids. Microbiology 146 (Pt 5), 1143-1149 (2000).] and/or species utilizing highly efficiency metabolic pathways such as but not limited to the reverse tricarboxylic acid cycle [i.e. reverse citric acid cycle] to fix carbon [Miura, A., Kameya, M., Arai, II., Ishii, M. & Igarashi, Y. A soluble NADH-dependent fumarate reductase in the reductive tricarboxylic acid cycle of *Hydrogenobacter thermophilus* TK-6. J Bacteriol 190, 7170-7177, doi:JB.00747-08 [pii] 10.1128/ JB.00747-08 (2008).; Shively, J. M., van Keulen, G. & Meijer, W. G. Something from almost nothing: carbon dioxide fixation in chemoautotrophs. Annu Rev Microbiol 52, 191-230, doi: 10.1146/annurev.micro.52.1.191 (1998).]. In terms of energy efficiency, the reverse tricarboxylic acid pathway can be a relatively favorable pathway. The synthesis of palmitic acid from $H_2$ and $CO_2$ is generally about 15% more efficient in terms of reducing equivalents consumed than palmitic acid synthesis in acetogens, due to the increased ATP output per reducing equivalent consumed in the oxyhydrogen reaction by oxyhydrogen microorganisms.

The source of inorganic carbon used in the chemosynthetic reaction process steps of certain embodiments of the present invention includes but is not limited to one or more of the following: a carbon dioxide-containing gas stream that may be pure or a mixture; liquefied $CO_2$; dry ice; dissolved carbon dioxide, carbonate ion, or bicarbonate ion in solutions including aqueous solutions such as sea water; inorganic carbon in a solid form such as a carbonate or bicarbonate minerals. Carbon dioxide and/or other forms of inorganic carbon can be introduced to the nutrient medium contained in reaction vessels either as a bolus addition, periodically, or continuously at the steps in the process where carbon-fixation occurs. Organic compounds containing only one carbon atom that can be used in the synthetic reaction process steps of certain embodiments of the present invention include but are not limited to one or more of the following: carbon monoxide, methane, methanol, formate, formic acid, and/or mixtures containing C1 chemicals including but not limited to various syngas compositions generated from various gasified or steam-reformed fixed carbon feedstocks.

In certain embodiments, organic compounds containing only one carbon atom and/or electron donors are generated through the gasification and/or pyrolysis of biomass and/or other organic matter (e.g., biomass and/or other organic matter from waste or low value sources), and provided as a syngas to the culture of oxyhydrogen microorganism, where the ratio of hydrogen to carbon monoxide in the syngas may or may not be adjusted through means such as the water gas shift reaction, prior to the syngas being delivered to the microbial culture. In certain embodiments, organic compounds containing only one carbon atom and/or electron donors are generated through methane steam reforming from methane or natural gas (e.g., stranded natural gas, or natural gas that would be otherwise flared or released to the atmosphere), or biogas, or landfill gas, and provided as a syngas to the culture of oxyhydrogen microorganism, where the ratio of hydrogen to carbon monoxide in the syngas may or may not be adjusted through means such as the water gas shift reaction, prior to the syngas being delivered to the microbial culture.

In certain embodiments of the present invention, carbon dioxide containing flue gases are captured from the smoke stack at temperature, pressure, and gas composition characteristic of the untreated exhaust, and directed with minimal modification into the reaction vessels where carbon-fixation occurs. In some embodiments in which impurities harmful to chemoautotrophic organisms are not present in the flue gas, modification of the flue gas upon entering the reaction vessels can be limited to the compression needed to pump the gas through the reactor system and/or the heat exchange needed to lower the gas temperature to one suitable for the microorganisms.

Oxyhydrogen microorganisms generally have an advantage over strict anaerobic acetogenic or methanogenic microorganisms for carbon capture applications due to the higher oxygen tolerance of oxyhydrogen microorganisms. Since industrial flue gas is one intended source of $CO_2$ for certain embodiments of the present invention, the relatively high oxygen tolerance of oxyhydrogen microorganisms, as compared with obligately anaerobic methanogens or acetogens, can allow the $O_2$ content of 2-6% found in typical fluegas to be tolerated.

In embodiments in which carbon dioxide bearing flue gas is transported through a system for dissolving the carbon dioxide into solution (such as is well known in the art of carbon capture), the scrubbed flue gas, (which generally primarily includes inert gases such as nitrogen), can be released into the atmosphere.

Gases in addition to carbon dioxide that are dissolved into solution and fed to the culture broth or dissolved directly into the culture broth in certain embodiments of the present invention include gaseous electron donors (e.g., hydrogen gas), but in certain embodiments of the present invention, may include other electron donors such as but not limited to carbon monoxide and other constituents of syngas, hydrogen sulfide, and/or other sour gases. A controlled amount of oxygen can also be maintained in the culture broth of some embodiments of the present invention, and in certain embodiments, oxygen will be actively dissolved into solution fed to the culture broth and/or directly dissolved into the culture broth.

The dissolution of oxygen, carbon dioxide, and/or electron donor gases such as but not limited to hydrogen and/or carbon monoxide into solution can be achieved in some embodiments of the present invention using a system of compressors, flowmeters, and/or flow valves known to one skilled in the art of bioreactor scale microbial culturing, which can be fed into one of more of the following commonly used systems for pumping gas into solution: sparging equipment; diffusers including but not limited to dome, tubular, disc, or doughnut geometries; coarse or fine bubble aerators; and/or venturi equipment. In certain embodiments of the present invention, surface aeration may also be performed using paddle aerators and the like. In certain embodiments of the present invention, gas dissolution is enhanced by mechanical mixing with an impeller and/or turbine. In some embodiments, hydraulic shear devices can be used to reduce bubble size.

In certain embodiments of the present invention that require the active pumping of air or oxygen into the culture broth in order to maintain favorable (e.g., optimal) oxygenation levels, oxygen bubbles are injected into the broth at a desirable (e.g., the optimal) diameter for mixing and oxygen transfer. This has been found to be 2 mm for certain embodiments [Environment Research Journal May/June 1999 pgs. 307-315]. In certain aerobic embodiments of the present invention, a process of shearing the oxygen bubbles is used to achieve this bubble diameter as described in U.S. Pat. No. 7,332,077. In some embodiments, bubbles have an average diameter of no larger than 7.5 mm and slugging is avoided.

In certain embodiments of the present invention utilizing hydrogen as electron donor, hydrogen gas is fed to the chemoautotrophic culture vessel by bubbling it through the culture medium and/or by diffusing it through a membrane that contacts the culture medium and is impermeable to the culture medium. The latter method is considered safer for many embodiments, and can be preferred since hydrogen accumulating in the gas phase can create explosive conditions (the range of explosive hydrogen concentrations in air is 4 to 74.5% and can he avoided in certain embodiments of the present invention). In some embodiments, the membrane is coated with a biofilm of the oxyhydrogen microorganisms such that the hydrogen must diffuse through the microorganism after passage through the membrane.

Additional chemicals required or useful for the maintenance and growth of oxyhydrogen microorganisms as known in the art can be added to the culture broth of certain embodiments of the present invention. These chemicals may include but are not limited to: nitrogen sources such as ammonia, ammonium (e g ammonium chloride ($NH_4Cl$), ammonium sulfate (($NH_4)_2SO_4$)), nitrate (e.g. potassium nitrate ($KNO_3$)), urea or an organic nitrogen source; phosphate (e.g. disodium phosphate ($Na_2HPO_4$), potassium phosphate ($KH_2PO_4$), phosphoric acid ($H_3PO_4$), potassium dithiophosphate ($K_3PS_2O_2$), potassium orthophosphate ($K_3PO_4$), dipotassium phosphate ($K_2HPO_4$)); sulfate; yeast extract; chelated iron; potassium (e.g. potassium phosphate ($KH_2PO_4$), potassium nitrate ($KNO_3$), potassium iodide (KI), potassium bromide (KBr)); and other inorganic salts, minerals, and trace nutrients (e.g. sodium chloride (NaCl), magnesium sulfate ($MgSO_4 \cdot 7H_2O$) or magnesium chloride ($MgCl_2$), calcium chloride ($CaCl_2$) or calcium carbonate ($CaCO_3$), manganese sulfate ($MnSO_4 \cdot 7H_2O$) or manganese chloride ($MnCl_2$), ferric chloride ($FeCl_3$), ferrous sulfate ($FeSO_4 \cdot 7H_2O$) or ferrous chloride ($FeCl_2 \cdot 4H_2O$), sodium bicarbonate ($NaHCO_3$) or sodium carbonate ($Na_2CO_3$), zinc sulfate ($ZnSO_4$) or zinc chloride ($ZnCl_2$), ammonium molybdate ($NH_4MoO_4$) or sodium molybdate ($Na_2MoO_4 \cdot 2H_2O$), cuprous sulfate ($CuSO_4$) or copper chloride ($CuCl_2 \cdot 2H_2O$), cobalt chloride ($CoCl_2 \cdot 6H_2O$), aluminum chloride ($AlCl_3 \cdot 6H_2O$), lithium chloride (LiCl), boric acid ($H_3BO_3$), nickel chloride $NiCl_2 \cdot 6H_2O$), tin chloride ($SnCl_2 \cdot H_2O$), barium chloride ($BaCl_2 \cdot 2H_2O$), copper selenate ($CuSeO_4 \cdot 5H_2O$) or sodium selenite ($Na_2SeO_3$), sodium metavanadate ($NaVO_3$), chromium salts). In certain embodiments the mineral salts medium (MSM) formulated by Schlegel et al may be used [*Thermophilic bacteria*, Jakob Kristjansson, Chapter 5, Section III, CRC Press, (1992)].

In certain embodiments, the concentrations of nutrient chemicals (e.g., the electron donors and acceptors), are maintained at favorable levels (e.g., as close as possible to their respective optimal levels) for enhanced (e.g., maximum) carbon uptake and fixation and/or production of organic compounds, which varies depending upon the oxyhydrogen species utilized but is known or determinable without undue experimentation to one of ordinary skill in the art of culturing oxyhydrogen microorganisms.

Along with nutrient levels, the waste product levels, pH, temperature, salinity, dissolved oxygen and carbon dioxide, gas and liquid flow rates, agitation rate, and pressure in the microbial culture environment are controlled in certain embodiments of the present invention. The operating parameters affecting carbon-fixation can be monitored with sensors (e.g. using a dissolved oxygen probe and/or an oxidation-reduction probe to gauge electron donor/acceptor concentrations) and can be controlled either manually or automatically based upon feedback from sensors through the use of equipment including but not limited to actuating valves, pumps, and agitators. The temperature of the incoming broth as well as incoming gases can be regulated by means such as but not limited to heat exchangers.

The dissolution of gases and nutrients needed to maintain the oxyhydrogen culture and promote carbon-fixation, as well as the removal of inhibitory waste products, can be enhanced by agitation of the culture broth. Oxyhydrogen microorganisms can carry out carbon-fixation reactions throughout the volume of the reaction vessel, which provides an advantage over other approaches including those that employ photosynthetic organisms, which are surface area limited due to the light requirements of photosynthesis. The use of agitation can further enhance this advantage by distributing the microorganisms, nutrients, optimal growth environment, and/or $CO_2$ as widely and evenly as possible throughout the reactor volume so that production is enhanced (e.g., the reactor volume in which carbon-fixation reactions occur at an optimal rate is maximized).

Agitation of the culture broth in certain embodiments of the present invention can be accomplished by equipment including but not limited to: recirculation of broth from the bottom of the container to the top via a recirculation conduit; sparging with carbon dioxide, electron donor gas (e.g. $H_2$), oxygen, and/or air; and/or a mechanical mixer such as but not limited to an impeller (100-1000 rpm) or turbine.

In certain embodiments of the present invention, the chemical environment, oxyhydrogen microorganisms, electron donors, electron acceptors, oxygen, pH, and/or temperature levels are varied either spatially and/or temporally over a series of bioreactors in fluid communication, such that a number of different carbon-fixation reactions and/or biochemical pathways to organic compounds are carried out sequentially or in parallel.

The nutrient medium containing oxyhydrogen microorganisms can be removed from the bioreactors in certain embodiments of the present invention partially or completely, periodically or continuously, and can be replaced with fresh cell-free medium, for example, to maintain the cell culture in an exponential growth phase, to maintain the cell culture in a growth phase (exponential or stationary) with enhanced (e.g., optimal) carbon-fixation rates, to replenish the depleted nutrients in the growth medium, and/or remove inhibitory waste products.

The high growth rate attainable by oxyhydrogen species can allow them to match or surpass the highest rates of carbon fixation and/or biomass production per standing unit biomass that can be achieved by photosynthetic microbes. Consequently, in certain embodiments, surplus biomass can be produced. Surplus growth of cell mass can be removed from the system to produce a biomass product. In some embodiments, surplus growth of cell mass can be removed from the system in order to maintain a desirable (e.g., an optimal) microbial population and cell density in the microbial culture for continued high carbon capture and fixation rates.

Another advantage of certain embodiments of the present invention relates to the vessels used to contain the carbon-fixation reaction environment and culture in the carbon capture and fixation process. Exemplary culture vessels that can be used in some embodiments of the present invention to culture and grow the oxyhydrogen microorganisms for carbon dioxide capture and fixation include those that are known to those of ordinary skill in the art of large scale microbial culturing. Such culture vessels, which may be of natural or artificial origin, include but are not limited to: airlift reactors; biological scrubber columns; bioreactors; bubble columns; caverns; caves; cisterns; continuous stirred tank reactors; counter-current, upflow, expanded-bed reactors; digesters and in particular digester systems such as known in the prior arts of sewage and waste water treatment or bioremediation; filters including but not limited to trickling filters, rotating biological contactor filters, rotating discs, soil filters; fluidized bed reactors; gas lift fermenters; immobilized cell reactors; lagoons; membrane biofilm reactors; microbial fuel cells; mine shafts; pachuca tanks; packed-bed reactors; plug-flow reactors; ponds; pools; quarries; reservoirs; static mixers; tanks; towers; trickle bed reactors; vats; vertical shaft bioreactors; and wells. The vessel base, siding, walls, lining, and/or top can be constructed out of one or more materials including but not limited to bitumen, cement, ceramics, clay, concrete, epoxy, fiberglass, glass, macadam, plastics, sand, sealant, soil, steels or other metals and their alloys, stone, tar, wood, and any combination thereof. In certain embodiments of the present invention where the oxyhydrogen microorganisms either require a corrosive growth environment and/or produce corrosive chemicals through the carbon-fixation reaction, corrosion resistant materials can be used to line the interior of the container contacting the growth medium.

Since oxyhydrogen microorganisms do not require sunlight in order to fix $CO_2$, they can be used in carbon capture and fixation processes that avoid many of the shortcomings that can be associated with photosynthetically based carbon capture and conversion technologies. For example, the maintenance of chemosynthesis does not require shallow, wide ponds, nor bioreactors with high surface area to volume ratios and special features like solar collectors or transparent materials. A technology such as certain embodiments of the present invention using oxyhydrogen microbes does not have the diurnal, geographical, meteorological, or seasonal constraints typically associated with photosynthetically based systems.

Certain embodiments of the present invention minimize material costs by using chemosynthetic vessel geometries having a low surface area to volume ratio, such as but not limited to cubic, cylindrical shapes with medium aspect ratio, ellipsoidal or "egg-shaped", hemispherical, or spherical shapes, unless material costs are superseded by other design considerations (e.g. land footprint size). The ability to use compact reactor geometries can arise from the absence of a light requirement for chemosynthetic reactions, in contrast to photosynthetic technologies where the surface area to volume ratio must be large to provide sufficient light exposure.

The oxyhydrogen microorganisms' lack of dependence on light also can allow plant designs with a much smaller footprint than those traditionally associated with photosynthetic approaches. For example, in scenarios where the plant footprint needs to be minimized due to restricted land availability, a long vertical shaft bioreactor system can be used for chemosynthetic carbon capture. A bioreactor of the long vertical shaft type is described, for example, in U.S. Pat. Nos. 4,279,754, 5,645,726, 5,650,070, and 7,332,077.

Unless superseded by other considerations, certain embodiments of the present invention minimize vessel surfaces across which high losses of water, nutrients, and/or heat occur, and/or the introduction of invasive predators into the reactor. The ability to minimize such surfaces can arise from the lack of light requirements for chemosynthesis. Photosynthetic based technologies generally are not able to minimize such surfaces since surfaces across which high losses of water, nutrients, and/or heat occur, as well as losses due to predation are generally the same surfaces across which the light energy necessary for photosynthesis is transmitted.

The culture vessels of the present invention can, in some embodiments, use reactor designs known to those of ordinary skill in the art of large scale microbial culture to maintain an aerobic, microaerobic, anoxic, anaerobic, or facultative environment depending upon the embodiment of the present invention. For example, similar to the design of many sewage treatment facilities, in certain embodiments of the present invention, tanks are arranged in a sequence, with serial forward fluid communication, where certain tanks are maintained in aerobic conditions and others are maintained in anaerobic conditions, in order to perform multiple chemosynthetic, and in certain embodiments, heterotrophic, processing steps on the carbon dioxide waste stream.

In certain embodiments of the present invention, the oxyhydrogen microorganisms are immobilized within their growth environment Immobilization of the microorganisms can be accomplished using any media known in the art of microbial culturing to support colonization by microorganisms including but not limited to growing the microorganisms on a matrix, mesh, or membrane made from any of a wide range of natural and synthetic materials and polymers including but not limited to one or more of the following: glass wool, clay, concrete, wood fiber, inorganic oxides such as $ZrO_2$, $Sb_2O_3$, or $Al_2O_3$, the organic polymer polysulfone, or open-pore polyurethane foam having high specific surface area. The microorganisms in certain embodiments of the present invention may also be grown on the surfaces of unattached objects distributed throughout the growth container as are known in the art of microbial culturing that include but are not limited to one or more of the following: beads; sand; silicates; sepiolite; glass; ceramics; small diameter plastic discs, spheres, tubes, particles, or other shapes known in the art; shredded coconut hulls; ground corn cobs; activated charcoal; granulated coal; crushed coral; sponge balls; suspended media; bits of small diameter rubber (elastomeric) polyethylene tubing; hanging strings of porous fabric, Berl saddles, Raschig rings. The materials used in the microbial support media may include hydrogen storage and/or electrode materials in order to enhance the transfer of reducing equivalents to the oxyhydrogen microorganisms. The electrode materials that can be used include but are not limited to one or more of the following: graphite, activated carbon, carbon nanofibers, conductive polymers, steel, iron, copper, titanium, lead, tin, palladium, platinum, transition metals, transition metal alloys, transition metal sulfides, oxides, chalcogenides, halides, hydroxides, oxyhydroxides, phosphates, sulfates, or carbonates. The hydrogen storage materials that may be used in this application include but are not limited to titanium, graphite, activated carbon, carbon nanofibers, iron, copper, lead, tin, metal hydrides including but not limited to $TiFeII_2$, $TiII_2$, $VII_2$, $ZrII_2$, $NiH$, $NbH_2$, $PdH$, and polymers known in the art of hydrogen storage including but not limited to Metal Organic Frameworks (MOF), and nanoporous polymeric materials. In certain embodiments, the hydrogen storage material does not react strongly with water or have a strong or rapid effect on the pII of the culture medium.

Inoculation of the oxyhydrogen culture into the culture vessel can be performed by methods including but not limited to transfer of culture from an existing oxyhydrogen culture inhabiting another carbon capture and fixation system of certain embodiments of the present invention and/or incubation from a seed stock raised in an incubator. The seed stock of oxyhydrogen strains can be transported and stored in forms including but not limited to a powder, a liquid, a frozen form, or a freeze-dried form as well as any other suitable form, which may be readily recognized by one skilled in the art. In certain embodiments in which a culture is established in a very large reactor, growth and establishment of cultures can be performed in progressively larger intermediate scale containers prior to inoculation of the full scale vessel.

The position of the process step or steps for the separation of cell mass from the process stream in the general process flow of certain embodiments of the present invention is illustrated in FIG. 1 by Box 5, labeled "Cell Separation".

Separation of cell mass from liquid suspension can be performed by methods known in the art of microbial culturing [Examples of cell mass harvesting techniques are given in International Patent Application No. WO08/00558, published Jan. 8, 1998; U.S. Pat. No. 5,807,722; U.S. Pat. No. 5,593,886 and U.S. Pat. No. 5,821,111.] including but not limited to one or more of the following: centrifugation; flocculation; flotation; filtration using a membranous, hollow fiber, spiral wound, or ceramic filter system; vacuum filtration; tangential flow filtration; clarification; settling; hydrocyclone. In certain embodiments where the cell mass is immobilized on a matrix, it can be harvested by methods including but not limited to gravity sedimentation or filtration, and separated from the growth substrate by liquid shear forces.

In certain embodiments of the present invention, if an excess of cell mass has been removed from the culture, it can be recycled back into the cell culture as indicated by the process arrow labeled "Recycled Cell Mass" in FIG. 1., along with fresh broth such that sufficient biomass is retained in the chemosynthetic reaction step or steps. This can allow for continued enhanced (e.g., optimal) autotrophic carbon-fixation and production of organic compounds. The cell mass recovered by the harvesting system can be recycled back into the culture vessel, for example, using an airlift or geyser pump. In certain embodiments, the cell mass recycled back into the culture vessel is not exposed to flocculating agents, unless those agents are non-toxic to the microorganisms.

In certain embodiments of the present invention, the microbial culture and carbon-fixation reaction is maintained using continuous influx and removal of nutrient medium and/or biomass, in steady state where the cell population and environmental parameters (e.g. cell density, chemical concentrations) are targeted at a constant (e.g., optimal) level over time. Cell densities can be monitored in certain embodiments of the present invention by direct sampling, by a correlation of optical density to cell density, and/or with a particle size analyzer. The hydraulic and biomass retention times can be decoupled so as to allow independent control of both the broth chemistry and the cell density. Dilution rates can be kept high enough so that the hydraulic retention time is relatively low compared to the biomass retention time, resulting in a highly replenished broth for cell growth. Dilution rates can be set at an optimal trade-off between culture broth replenishment, and increased process costs from pumping, increased inputs, and other demands that rise with dilution rates.

To assist in the processing of the biomass product into biofuels or other useful products, the surplus microbial cells in certain embodiments of the invention can be broken open following the cell recycling step using, for example, methods including but not limited to ball milling, cavitation pressure, sonication, or mechanical shearing.

The harvested biomass in some embodiments can be dried in the drying step or steps of Box 7, labeled "Dryer" in the general process flow of certain embodiments of the present invention illustrated in FIG. 1.

Surplus biomass drying can be performed in certain embodiments of the present invention using technologies including but not limited to centrifugation, drum drying, evaporation, freeze drying, heating, spray drying, vacuum drying, and/or vacuum filtration. Heat waste from the industrial source of flue gas can be used in drying the biomass, in certain embodiments. In addition, the chemosynthetic oxidation of electron donors is generally exothermic and generally produces waste heat. In certain embodiments of the present invention waste heat can be used in drying the biomass.

In certain embodiments of the invention, the biomass is further processed following drying to aid the production of biofuels or other useful chemicals through the separation of the lipid content or other targeted biochemicals from the microbial biomass. The separation of the lipids can be performed by using nonpolar solvents to extract the lipids such as, but not limited to, hexane, cyclohexane, ethyl ether, alcohol (isopropanol, ethanol, etc.), tributyl phosphate, supercritical carbon dioxide, trioctylphosphine oxide, secondary and tertiary amines, or propane. Other useful biochemicals can be extracted using solvents including but not limited to: chloroform, acetone, ethyl acetate, and tetrachloroethylene.

The extracted lipid content of the biomass can be processed using methods known in the art and science of biomass refining including but not limited to one or more of the following—catalytic cracking and reforming; decarboxylation; hydrotreatment; isomerization—to produce petroleum and petrochemical replacements, including but not limited to one or more of the following: JP-8 jet fuel, diesel, gasoline, and other alkanes, olefins and aromatics. In some embodiments, the extracted lipid content of the biomass can be converted to ester-based fuels, such as biodiesel (fatty acid methyl ester or fatty acid ethyl ester), through processes known in the art and science of biomass refining including but not limited to transesterification and esterification.

The broth left over following the removal of cell mass can be pumped to a system for removal of the chemical products of chemosynthesis and/or spent nutrients which are recycled or recovered to the extent possible and/or disposed of.

The position of the process step or steps for the recovery of chemical products from the process stream in the general process flow of certain embodiments of the present invention is illustrated in FIG. 1 by Box 8, labeled "Separation of chemical co-products."

Recovery and/or recycling of chemosynthetic chemical products and/or spent nutrients from the aqueous broth solution can be accomplished in certain embodiments of the present invention using equipment and techniques known in the art of process engineering, and targeted towards the chemical products of particular embodiments of the present invention, including but not limited to: solvent extraction; water extraction; distillation; fractional distillation; cementation; chemical precipitation; alkaline solution absorption; absorption or adsorption on activated carbon, ion-exchange resin or molecular sieve; modification of the solution pH and/or oxidation-reduction potential, evaporators, fractional crystallizers, solid/liquid separators, nanofiltration, and all combinations thereof.

In certain embodiments of the present invention, free fatty acids, lipids, or other medium or long chain organic compounds appropriate for refinement to biofuel products that have been produced through chemosynthesis can be recovered from the process stream at the step at Box 8 in FIG. 1. These free organic molecules can be released into the process stream solution from the oxyhydrogen microorganisms through means including but not limited to cellular excretion or secretion or cell lysis. In certain embodiments of the present invention, the recovered organic compounds are processed using methods known in the art and science of biomass refining including but not limited to one or more of the following: catalytic cracking and reforming; decarboxylation; hydrotreatment; isomerization. Such processes can be used to produce petroleum and petrochemical replacements, including but not limited to one or more of the following: JP-8 jet fuel, diesel, gasoline, and other alkanes, olefins and aromatics. Recovered fatty acids can be converted to ester-based fuels, such as biodiesel (fatty acid methyl ester or fatty acid ethyl ester), through processes known in the art and science of biomass refining including but not limited to transesterification and esterification.

In some embodiments, following the recovery of chemical products from the process stream, the removal of the waste products is performed as indicated by Box 9, labeled "Waste removal" in FIG. 1. The remaining broth can be returned to the culture vessel along with replacement water and/or nutrients.

In certain embodiments of the present invention involving chemoautotrophic oxidization of electron donors extracted from a mineral ore, a solution of oxidized metal cations can remain following the chemosynthetic reaction steps. A solution rich in dissolved metal cations can also result from a particularly dirty flue gas input to the process such as from a coal fired plant. In some such embodiments of the present invention, the process stream can be stripped of metal cations by methods including but not limited to: cementation on scrap iron, steel wool, copper or zinc dust; chemical precipitation as a sulfide or hydroxide precipitate; electrowinning to plate a specific metal; absorption on activated carbon or an ion-exchange resin, modification of the solution pH and/or oxidation-reduction potential, solvent extraction. In certain embodiments of the present invention, the recovered metals can be sold for an additional stream of revenue.

In certain embodiments, the chemicals that are used in processes for the recovery of chemical products, the recycling of nutrients and water, and the removal of waste have low toxicity for humans, and if exposed to the process stream that is recycled back into the growth container, low toxicity for the oxyhydrogen microorganisms being used.

In certain embodiments of the present invention, the pH of the microbial culture is controlled. To address a decrease in pH, a neutralization step can be performed prior to recycling the broth back into the culture vessel in order to maintain the pH within an optimal range for microbial maintenance and growth. Neutralization of acid in the broth can be accomplished by the addition of bases including but not limited to: limestone, lime, sodium hydroxide, ammonia, caustic potash, magnesium oxide, iron oxide. In certain embodiments, the base is produced from a carbon dioxide emission-free source such as naturally occurring basic minerals including but not limited to calcium oxide, magnesium oxide, iron oxide, iron ore, olivine containing a metal oxide, serpentine containing a metal oxide, ultramafic deposits containing metal oxides, and underground basic saline aquifers. If limestone is used for neutralization, then carbon dioxide will generally be released, which can be directed back into the growth container for uptake by chemosynthesis and/or sequestered in some other way, rather than released into the atmosphere.

An additional feature of certain embodiments of the present invention relates to the uses of organic compounds and/or biomass produced through the chemosynthetic process step or steps of certain embodiments of the present invention. Uses of the organic compounds and/or biomass produced include but are not limited to: the production of liquid fuels including but not limited to JP-8 jet fuel, diesel, gasoline, octane, biodiesel, butanol, ethanol, propanol, isopropanol, propane, alkanes, olefins, aromatics, fatty alcohols, fatty acid esters, alcohols; the production of organic chemicals including but not limited to 1,3-propanediol, 1,3-butadiene, 1,4-butanediol, 3-hydroxypropionate, 7-ADCA/cephalosporin, ε-caprolactone, γ-valerolactone, acrylate, acrylic acid, adipic acid, ascorbate, aspartate, ascorbic acid, aspartic acid, caprolactam, carotenoids, citrate, citric acid, DHA, docetaxel, erythromycin, ethylene, gamma butyrolactone, glutamate, glutamic acid, HPA, hydroxybutyrate, isopentenol, isoprene, isoprenoids, itaconate, itaconic acid, lactate, lactic acid, lanosterol, levulinic acid, lycopene, lysine, malate, malonic acid, peptides, omega-3 DHA, omega fatty acids, paclitaxel, PHA, PHB, polyketides, polyols, propylene, pyrrolidones, serine, sorbitol, statins, steroids, succinate, terephthalate, terpenes, THF, rubber, wax esters, polymers, commodity chemicals, industrial chemicals, specialty chemicals, paraffin replacements, additives, nutritional supplements, neutraceuticals, pharmaceuticals, pharmaceutical intermediates, personal care products; as raw material and/or feedstock for manufacturing or chemical processes; as feed stock for alcohol or other biofuel fermentation and/or gasification and liquefaction processes and/or other biofuel production processes including but not limited to catalytic cracking, direct liquefaction, Fisher Tropsch processes, hydrogenation, methanol synthesis, pyrolysis, transesterification, or microbial syngas conversions; as a biomass fuel for combustion in particular as a fuel to be co-fired with fossil fuels; as sources of pharmaceutical, medicinal or nutritional substances; as a carbon source for large scale fermentations to produce various chemicals including but not limited to commercial enzymes, antibiotics, amino acids, vitamins, bioplastics, glycerol, or 1,3-propanediol; as a nutrient source for the growth of other microbes or organisms; as feed for animals including but not limited to cattle, sheep, chickens, pigs, or fish; as feed stock for methane or biogas production; as fertilizer; soil additives and soil stabilizers.

An additional feature of certain embodiments of the present invention relates to the optimization of oxyhydrogen microorganisms for carbon dioxide capture, carbon fixation into organic compounds, and the production of other valuable chemical co-products. This optimization can occur through methods known in the art of artificial breeding including but not limited to accelerated mutagenesis (e.g. using ultraviolet light or chemical treatments), genetic engineering or modification, hybridization, synthetic biology or traditional selective breeding. For certain embodiments of the present invention utilizing a consortium of microorganisms, the community can be enriched with desirable oxyhydrogen microorganisms using methods known in the art of microbiology through growth in the presence of targeted electron donors including but not limited to hydrogen, acceptors including but not limited to oxygen, and environmental conditions.

An additional feature of certain embodiments of the present invention relates to modifying biochemical pathways in oxyhydrogen microorganisms for the production of targeted organic compounds. This modification can be accomplished by manipulating the growth environment and/or through methods known in the art of artificial breeding including but not limited to accelerated mutagenesis (e.g. using ultraviolet light or chemical treatments), genetic engineering or modification, hybridization, synthetic biology or traditional selective breeding. The organic compounds produced through the modification include but are not limited to one or more of the following: biofuels including but not limited to JP-8 jet fuel, diesel, gasoline, biodiesel, butanol, ethanol, long chain hydrocarbons, lipids, fatty acids, pseudovegetable oil, and methane produced from biological reactions in vivo; or organic compounds and/or biomass optimized as a feedstock for biofuel and/or liquid fuel production through chemical post-processing. These forms of fuel can be used as renewable/alternate sources of energy with low greenhouse gas emissions.

In order to give specific examples of the overall biological and chemical process for using oxyhydrogen microorganisms to capture $CO_2$ and produce biomass and other useful co-products, a process flow diagram describing a specific embodiment of the present invention is now provided and described. This specific example should not be construed as limiting the present invention in any way and is provided for the sole purpose of illustration.

Figure 2:
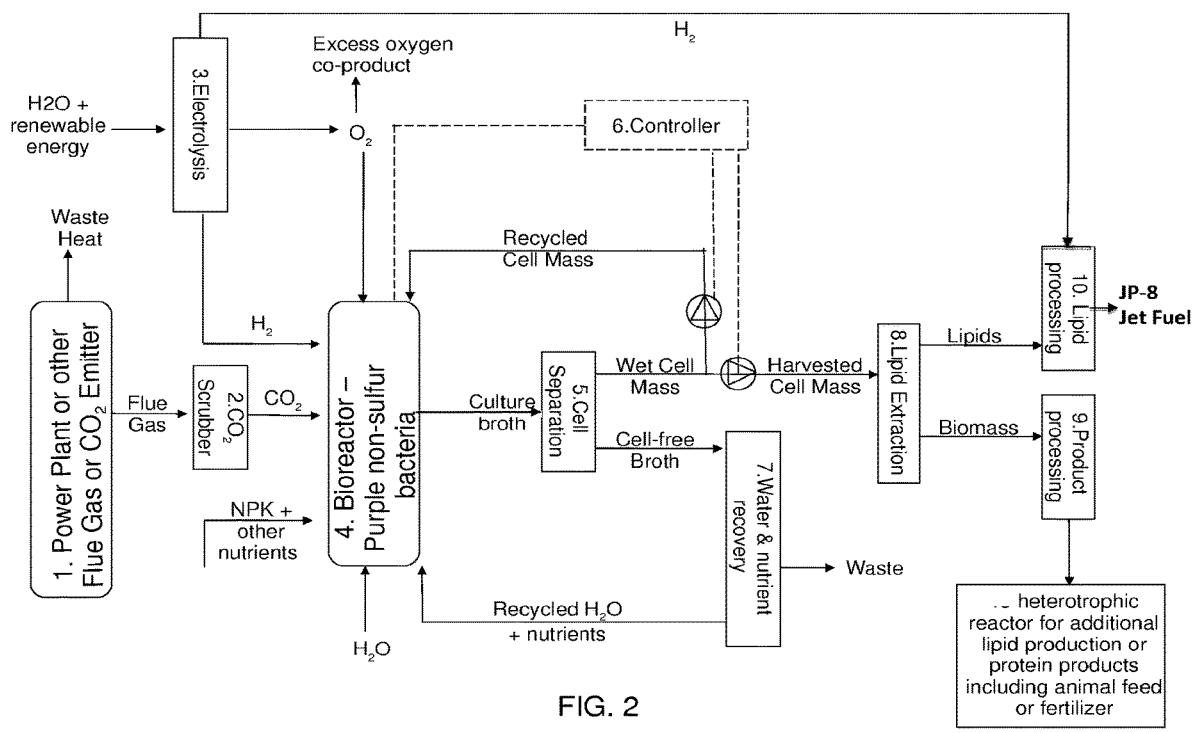
FIG. 2 is a process flow diagram for another embodiment of the present invention with capture of CO$_2$ performed by a microorganism capable of performing an oxyhydrogen reaction (e.g., hydrogen oxidizing purple non-sulfur bacteria) to produce a lipid-rich biomass that is converted into JP-8 jet fuel.

FIG. 2 includes an exemplary process flow diagram illustrating one embodiment of the present invention for the capture of $CO_2$ by oxyhydrogen microorganisms and the production of lipid rich biomass, which is converted to JP-8 jet fuel. In this set of embodiments, a carbon dioxide-rich flue gas is captured from an emission source such as a power plant, refinery, or cement producer. The flue gas can then be compressed and pumped into cylindrical anaerobic digesters containing one or more oxyhydrogen microorganisms such as but not limited to: purple non-sulfur photosynthetic bacteria including but not limited to *Rhodopseudomonas palustris, Rhodopseudomonas capsulata, Rhodopseudomonas viridis, Rhodopseudomonas sulfoviridis, Rhodopseudomonas blastica,* and other *Rhodopseudomonas* sp.

In some embodiments, *Rhodopseudomonas capsulata* can be used as the oxyhydrogen microorganism, and, in some cases, a doubling time of 6 hours for chemoautotrophic growth on hydrogen can be achieved. See, for example, Madigan, Gest, *J. Bacteriology* (1979) 524-530, which is incorporated herein by reference. In some embodiments, the microbial doubling time can be less than 6 hours, or shorter. In some embodiments, the dry biomass concentration can be at least about 3 g/l, at least about 4 g/l, or at least 5 g/l at steady state. In some embodiments, the biomass lipid content in the oxyhydrogen microorganism can be at least about 10%, at least about 20%, at least about 30%, at least about 35%, or at least about 40%. For example, in some embodiments, *Rhodopseudomonas palustris* can be used as the oxyhydrogen microorganism. See, for example, Carlozzi, Pintucci, Piccardi, Buccioni, Minieri, Lambardi, *Biotechnol. Lett.,* (2009) DOI 10.1007/s10529-009-0183-2, which is incorporated herein by reference. In certain embodiments, the biomass lipid content of the oxyhydrogen microorganisms is at least 40%; there is a steady state bioreactor cell density of at least 5 g/liter in a continuous process; the microbial doubling time is at most 6 hours; the process achieves at least a 40% energy efficiency in converting hydrogen into biomass; and/or at least 60% of the biomass energy content is stored as lipid (which corresponds to about 40% biomass lipid content by weight).

In the set of embodiments illustrated in FIG. 2, hydrogen electron donor and oxygen and carbon dioxide electron acceptors are added continuously to the growth broth along with other nutrients required for chemosynthesis and culture maintenance and growth that are pumped into the digester. In certain embodiments, the hydrogen source is a carbon dioxide emission-free process. Exemplary carbon dioxide emission-free processes include, for example, electrolytic or thermochemical processes powered by energy technologies including but not limited to photovoltaics, solar thermal, wind power, hydroelectric, nuclear, geothermal, enhanced geothermal, ocean thermal, ocean wave power, tidal power. In the set of embodiments illustrated in FIG. 2, oxygen serves as an electron acceptor in the chemosynthetic reaction for the intracellular production of ATP through the oxyhydrogen reaction linked to oxidative phosphorylation. The oxygen can originate from the flue gas, it can be generated from the water-splitting reaction used to produce the hydrogen, and/or it can be taken from air. In FIG. 2, carbon dioxide from the flue gas serves as an electron acceptor for the synthesis of organic compounds through biochemical pathways utilizing the ATP produced through the oxyhydrogen reaction and NADH and/or NADPH produced from the intracellular enzymatically catalyzed reduction of $NAD^+$ or $NADP^+$ by $H_2$. The culture broth can be continuously removed from the digesters and flowed through membrane filters to separate the cell mass from the broth. The cell mass can then be recycled back into the digesters and/or pumped to post-processing where lipid extraction is performed according to methods known to those skilled in the art. The lipids can then be converted to JP-8 jet fuel using methods known to those skilled in the art of biomass refining (see, for example, U.S. DOE Energy Efficiency & Renewable Energy Biomass Program, "National Algal Biofuels Technology Roadmap", May 2010, which is incorporated herein by reference in its entirety. Cell-free broth which has passed through the cell mass removing filters can then be subjected to any necessary additional waste removal treatments which depends on the source of flue gas. The remaining water and nutrients can then be pumped back into the digesters.

Some of the *Rhodopseudomonas* species have extremely versatile metabolisms, making them capable of photoautotrophic, photoheterotrophic, heterotrophic, as well as chemoautotrophic growth and the ability to live in both aerobic and anaerobic environments [Madigan, Gest, J. Bacteriology (1979) 524-530]. In certain embodiments of the present invention the heterotrophic capability of *Rhodopseudomonas* sp. is exploited to further improve the efficiency of energy and carbon conversion to lipid product. The non-lipid biomass remainder following lipid extraction is composed of primarily protein and carbohydrate. In certain embodiments of the present invention, some of the carbohydrate and/or protein remainder following lipid extraction is acid hydrolyzed to simple sugars and/or amino acids, the acid is neutralized, and the solution of simple sugars and/or amino acids are fed to a second heterotrophic bioreactor containing *Rhodopseudomonas* sp. that consumes the biomass input and produces additional lipid product, as illustrated in FIG. 2.

The *Rhodopseudomonas palustris* genome has been sequenced by the DOE Joint Genome Institute [Larimer et. al (2003) Nature Biotechnology 22, 55-61]. It is reported that its genetic system is particularly amenable to modification. In one set of embodiments of the present invention the carbon-fixation reaction or reactions are performed by

*Rhodopseudomonas* sp. that have been improved, optimized or engineered for the improved fixation of carbon dioxide and/or other forms of inorganic carbon and/or the improved production of organic compounds through methods including but not limited to one or more of the following: accelerated mutagenesis, genetic engineering or modification, hybridization, synthetic biology or traditional selective breeding.

Figure 3:
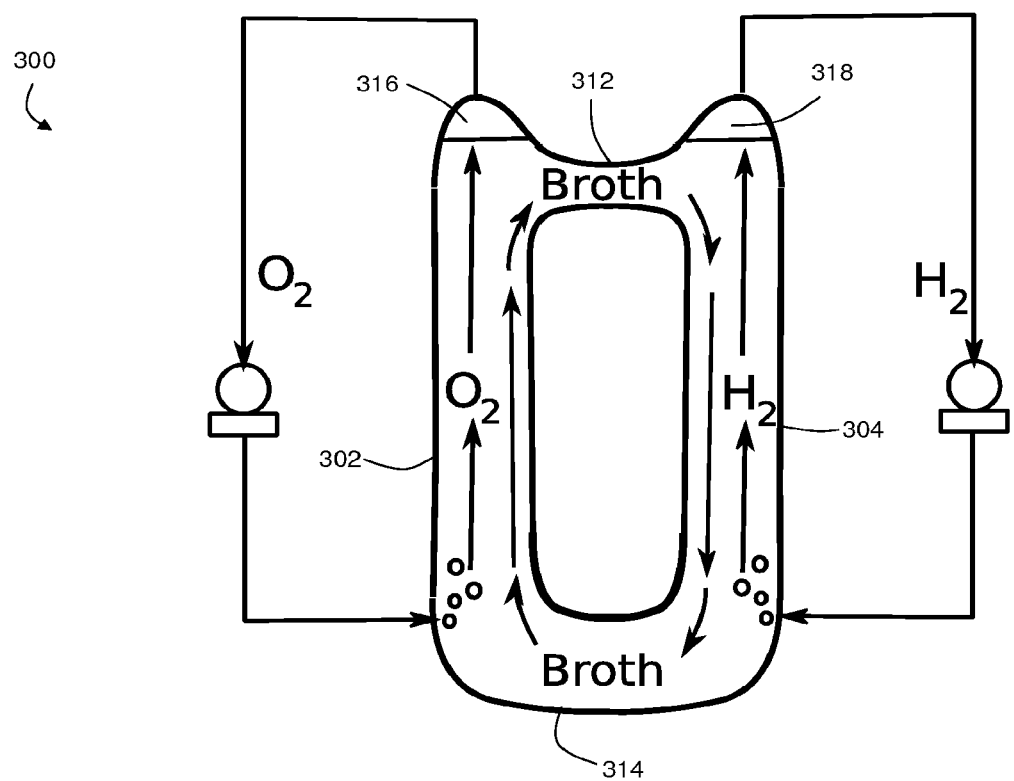
FIG. 3 is diagram of a bioreactor design that can avoid dangerous mixtures of hydrogen and oxygen by exploiting the low solubilities of hydrogen and oxygen gas in water while providing the oxyhydrogen microorganism with the oxygen and hydrogen needed for cellular energy and carbon fixation.

FIG. 3 includes an exemplary schematic diagram of a bioreactor 300, which can be used in certain embodiments. Bioreactor 300 can be used, for example, as the reactor illustrated as Box 4 in FIG. 1 labeled "Bioreactor—Knallgas Microbes" and/or as the reactor illustrated as Box 4 in FIG. 2 labeled "Bioreactor—Purple non-sulfur bacterial." Bioreactor 300 illustrated in FIG. 3 can be operated to take advantage of the low solubilities of hydrogen and oxygen gas in water and avoids dangerous mixtures of hydrogen and oxygen gas. In addition, the bioreactor can provide the oxyhydrogen microorganisms with the oxygen and hydrogen needed for cellular energy and carbon fixation, for example, by sparging, bubbling, or diffusing oxygen or air up a vertical liquid column filled with culture medium.

Bioreactor 300 includes a first column 302 and a second column 304. In the set of embodiments illustrated in FIG. 3, oxygen is introduced to first column 302 while hydrogen or syngas is introduced to second column 304, although in other embodiments, their order may be reversed. The oxygen and/or hydrogen and/or syngas can be introduced to their respective columns by, for example, sparging, bubbling, and/or diffusion such that they travel upwards through the culture medium. Bioreactor 300 can include a horizontal liquid connection 312 at the top of the columns and a horizontal liquid connection 314 at the bottom of the columns.

In some embodiments, the level of the liquid medium with column 302 is maintained such that gaseous headspace 316 is formed above the liquid. In addition, in some cases, the level of liquid medium within column 304 can be arranged such that gaseous headspace 318 is formed above the liquid medium. In some embodiments, headspace 316 and/or headspace 318 can occupy at least about 2%, at least about 10%, at least about 25%, between 2% and about 80%, between about 10% and about 80%, or between about 25% and about 80% of the total volume of the column in which they are positioned. Headspaces 316 and 318 can be isolated from each other by the liquid medium. In some embodiments, the low solubility of the gases in the liquid medium allow for the collection of gases at the tops of the columns after bubbling or diffusing the gases up through their respective columns. Establishing isolated headspaces can prevent a dangerous amount of hydrogen and oxygen gases from mixing with each other. For example, the hydrogen gas in one column can be prevented from mixing with the oxygen gas in other column (and vice versa). Inhibiting mixing of the hydrogen and oxygen gases can be achieved, for example, by maintaining the connections between the two columns such that they are filled with liquid, thereby preventing transport of the gases from one column to the other. In some embodiments, headspaces 316 and/or 318 can remain substantially stationary at the top of their respective columns as liquid medium is circulated between the first and second columns.

In FIG. 3, the horizontal liquid connection 312 at the top of the columns and horizontal liquid connection 314 bottom of the columns are arranged such that they allow the liquid medium to flow up one column in the direction of the oxygen gas, and down the other column, countercurrent to the hydrogen gas and/or syngas while the horizontal liquid connections remain continuously filled. In other embodiments, the liquid medium can flow up the column containing the hydrogen gas and/or syngas and down the other column containing the oxygen gas(in countercurrent flow relative to the gas).

In some embodiments, the gas on one side or the other, but not both sides simultaneously, may be bubbled forcefully such that that particular column acts as an airlift reactor and drives the circulation of the culture medium between the two columns. In some embodiments, the circulation of the fluid may also be assisted by impellers, turbines, and/or pumps.

In some such embodiments, any unused hydrogen gas and/or syngas that passes through the culture medium without being taken up by the microorganisms (and which may end up in the head space) can be recirculated by pumping the gas out of the head space, optionally compressing it, and pumping it back into the medium at the bottom of the liquid column on the hydrogen and/or syngas side. In some embodiments, the oxygen and/or air might be similarly be recirculated on its respective side or alternatively vented after passing through the headspace.

The oxyhydrogen microorganisms are allowed to freely circulate along with the liquid medium between the first and second columns in certain embodiments. In other embodiments, the oxyhydrogen microorganisms are restricted to the hydrogen side, for example, by using a microfilter that retains the microorganisms on the hydrogen side but allows the liquid medium to pass through.

Figure 4:
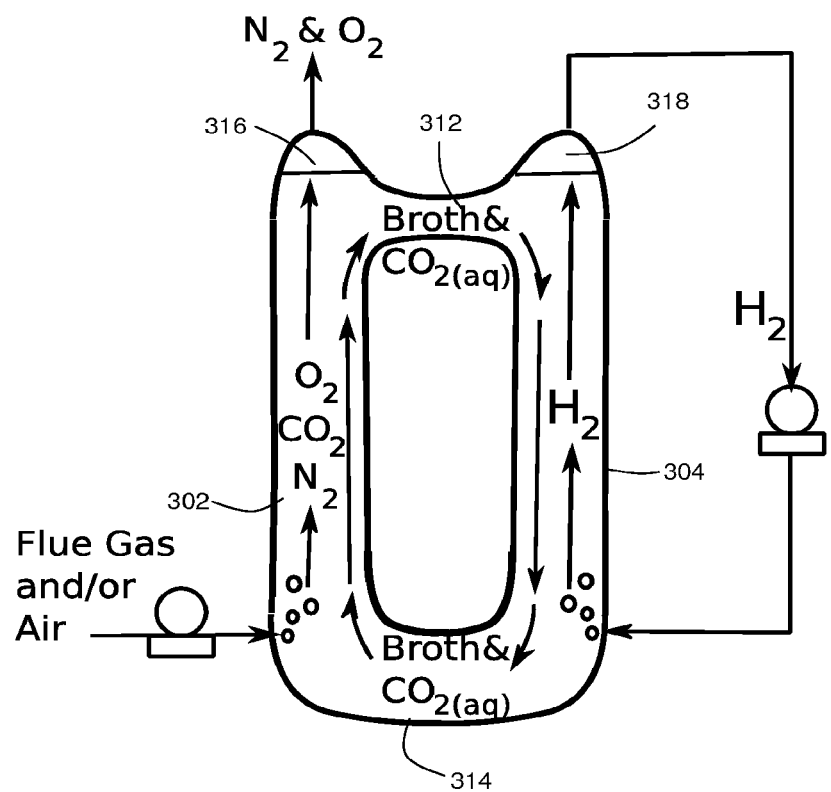
FIG. 4 is a diagram of a bioreactor design that takes advantage of the relatively high solubility of carbon dioxide and the strong ability of oxyhydrogen microorganism to capture carbon dioxide from relatively dilute streams using a carbon concentrating mechanism (CCM), to remove CO$_2$ from a dilute gas mixture and separate it from low solubility gases such as oxygen and nitrogen.

FIG. 4 includes an exemplary schematic illustration of another method of operating bioreactor 300 that can be used in certain embodiments. The bioreactor arrangement in FIG. 4 can take advantage of the relatively high solubility of carbon dioxide and/or the strong ability of oxyhydrogen microorganism to capture carbon dioxide from relatively dilute streams. The operation illustrated in FIG. 4 can exploit the carbon concentrating mechanism native to oxyhydrogen microorganisms. Flue gas and/or air containing carbon dioxide can be transported through the oxygen side of the bioreactor. The carbon dioxide can be dissolved into solution and/or taken up by the oxyhydrogen microbes and subsequently transported over to the hydrogen side of the reactor, for example, through the horizontal liquid connection 312 at the top of the column. On the hydrogen side, reducing equivalents can be provided that drive fixation of the carbon. In some embodiments, other gases pumped in on the oxygen side (e.g., oxygen, nitrogen, etc.) have a low solubility relative to $CO_2$, and are not carried over to the hydrogen side. Rather than being passed from column 302 to column 304, the low solubility gases can be transported to headspace 316. In some embodiments, after the gases are transported to headspace 316, they can be vented.

Figure 5:
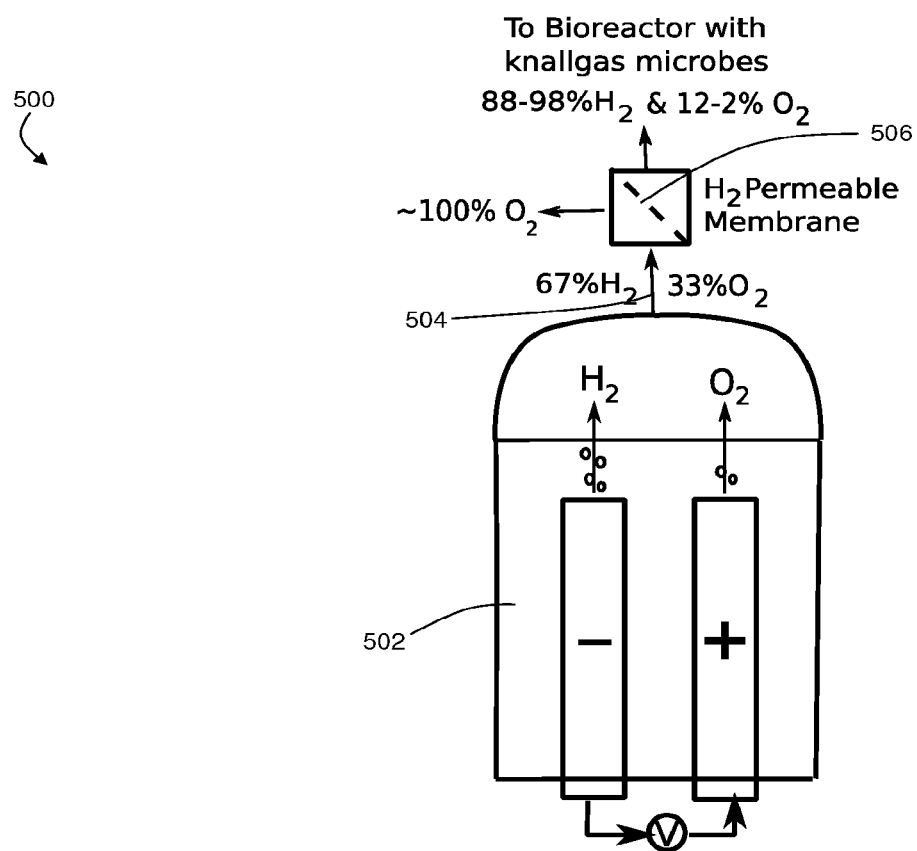
FIG. 5 is an electrolysis technology that is specially designed to take advantage of the oxyhydrogen microorganisms' tolerance and need for a certain concentration of oxygen by decreasing the complete separation of the hydrogen and oxygen produced from standard electrolysis.

FIG. 5 includes an exemplary schematic diagram of an electrolysis apparatus 500, which can be used in certain embodiments. Electrolysis apparatus 500 can be used, for example, as the unit illustrated as Box 3 in FIG. 1 labeled "Electron donor generation" and/or as the unit illustrated as Box 3 in FIG. 2 labeled "Electrolysis." Electrolysis apparatus 500 can be designed to take advantage of the oxyhydrogen microorganisms' tolerance and need for a certain concentration of oxygen by decreasing or eliminating the complete separation of the hydrogen and oxygen produced from the electrolysis step, relative to the separation schemes employed in conventional electrolysis systems designed for the production of pure hydrogen. Apparatus 500 includes an electrolysis unit 502 that is configured to generate $H_2$ and $O_2$ from water. Any suitable electrolysis unit 502 can be employed to perform the electrolysis step. In some embodiments, the electrical resistance in electrolysis unit 502 can be reduced at the expense of complete hydrogen and oxygen separation by means including but not limited one or more of the following: removing the separator used to prevent gas crossover in standard electrolyzers and/or using a relatively short distance between positive and negative electrodes.

Apparatus 500 can include an outlet 504, through which the hydrogen and oxygen produced by the electrolysis unit 502 can be transported. Outlet 504 can be equipped with a separator 506, which can be used to separate at least a portion of the hydrogen from at least a portion of the oxygen. In certain embodiments, semipermeable membranes such as polymer membranes designed for $H_2$ separation can be employed as separator 506. In certain embodiments, separator 506 can include metal foils including but not limited to foils made from palladium, palladium alloys, vanadium, niobium, tantalum and their alloys, and/or other metals and/or alloys that are permeable to hydrogen but less permeable to other gases such as oxygen. In some embodiments, the separator can be used to separate the hydrogen from the oxygen such that the hydrogen content of one gas product exiting the separator is enriched to a level that is desirable for oxyhydrogen microbes. The gas product can then be transported to a bioreactor, where it can be used as a feedstock. In certain embodiments, the amount of hydrogen in one of the gas products exiting the separator can be set at a level such that oxyhydrogen microorganism activity is maximized, and the loss of hydrogen produced through electrolysis apparatus 500 is minimized The following documents are incorporated herein by reference in their entirety for all purposes: U.S. Provisional Patent Application No. 61/328,184, filed Apr. 27, 2010 and entitled "USE OF OXYHYDROGEN MICROORGANISMS FOR NON-PHOTOSYNTHETIC CARBON CAPTURE AND CONVERSION OF INORGANIC CARBON SOURCES INTO USEFUL ORGANIC COMPOUNDS"; International Patent Application Serial No. PCT/US2010/001402, filed May 12, 2010, entitled "BIOLOGICAL AND CHEMICAL PROCESS UTILIZING CHEMOAUTOTROPHIC MICROORGNISMS FOR THE CHEMOSYTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS"; and U.S. Patent Application Publication No. 2010/0120104, filed Nov. 6, 2009, entitled "BIOLOGICAL AND CHEMICAL PROCESS UTILIZING CHEMOAUTOTROPHIC MICROORGNISMS FOR THE CHEMOSYTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS.

The following examples are intended to illustrate certain embodiments of the present invention, but do not exemplify the full scope of the invention.

EXAMPLE 1

In this example, oxyhydrogen microorganisms that accumulate high lipid content and/or other valuable compounds such as polyhydroxybutyrate (PIIB) to are grown on an inorganic medium with $CO_2$ as the carbon source and hydrogen acting as the electron donor while oxygen provides the electron acceptor. Oxyhydrogen microbes such as these can be used in certain embodiments of the present invention in converting C1 chemicals such as carbon dioxide into longer chain organic chemicals.

Static anaerobic reaction vessels were inoculated with *Cupriavidus necator* DSM 531 (which can accumulate a high percentage of cell mass as PHB). The inoculum were taken from DSM medium no. 1 agar plates kept under aerobic conditions at 28 degrees Celsius. Each anaerobic reaction vessel had 10 ml of liquid medium DSM no. 81 with 80% $H_2$, 10% $CO_2$ and 10% $O_2$ in the headspace. The cultures were incubated at 28 degrees Celsius. The *Cupriavidus necator* reached an optical density (OD) at 600 nm of 0.98 and a cell density of $4.7 \times 10^8$ cells/ml after 8 days.

Another growth experiment was performed for *Cupriavidus necator* (DSM 531). The medium used for growth was the mineral salts medium (MSM) formulated by Schlegel et al. The MSM medium was formed by mixing 1000 ml of Medium A, 10 ml of Medium B, and 10 ml of Medium C. Medium A included 9 g/l $Na_2HPO_4 \cdot 12H_2O$, 1.5 g/l $KH_2PO_4$, 1.0 g/l, 0.2 g/l $MgSO_4 \cdot 7H_2O$, and 1.0 ml of Trace Mineral Medium. The Trace Mineral Medium included 1000 ml distilled water; 100 mg/l $ZnSO_4 \cdot 7H_2O$; 30 mg/l $MnCl_2 \cdot 4H_2O$; 300 mg/l $H_3BO_3$; 200 mg/l $COCl_2 \cdot 6H_2O$; 10 mg/l $CuCl_2 \cdot 2H_2O$; 20 mg/l $NiCl_2 \cdot 6H_2O$; and 30 mg/l $Na_2MoO_4 \cdot 2H_2O$. Medium B contained 100 ml of distilled water; 50 mg ferric ammonium citrate; and 100 mg $CaCl_2$. Medium C contained 100 ml of distilled water and 5 g $NaHCO_3$.

The cultures were grown in 20 ml of MSM media in 150-ml stopped and sealed serum vials with the following gas mixture in the headspace: 71% Hydrogen; 4% Oxygen; 16% Nitrogen; 9% Carbon dioxide. The headspace pressure was 7 psi. The cultures were grown for eight days at 30 degrees Celsius. *Cupriavidus necator* reached an OD at 600 nm of 0.86.

It is known that, in larger scale bioreactor equipment, faster growth rates and higher cell densities can be attained. Accordingly, it is believed that higher growth rates and cell densities can be achieved simply by scaling up the systems described above. For example *Cupriavidus necator* which is also known as *Alcaligenes eutrophus, Ralstonia eutropha, Hydrogenomona eutropha,* has been grown in bioreactors on $H_2/CO_2/O_2$ to a cell density of over 90 grams/liter [Tanaka, Ishizaki; Biotech. And Bioeng., vol. 45, 268-275 (1995)], and with doubling times below two hours [Ammann, Reed, Durichek, Appl. Microbio., (1968) 822-826].

Specific preferred embodiments of the present invention have been described here in sufficient detail to enable those skilled in the art to practice the full scope of invention. However it is to be understood that many possible variations of the present invention, which have not been specifically described, still fall within the scope of the present invention and the appended claims. Hence these descriptions given herein are added only by way of example and are not intended to limit, in any way, the scope of this invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

What is claimed is:

1. A biological and chemical method for the capture and conversion of an inorganic carbon compound and/or an organic compound containing only one carbon atom into biomass and/or biochemicals, comprising:
introducing a carbon source consisting of an inorganic carbon compound and/or an organic compound containing only one carbon atom into a bioreactor comprising an environment that comprises a liquid culture medium suitable for maintaining oxyhydrogen microorganisms and/or capable of maintaining extracts of oxyhydrogen microorganisms, wherein the liquid culture medium comprises nitrogen and phosphorous; and
converting the inorganic carbon compound and/or the organic compound containing only one carbon atom into biomass and/or biochemicals within the environment via at least one chemosynthetic carbon-fixing reaction utilizing oxyhydrogen microorganisms belonging to the genus *Cupriavidus* and/or cell extracts containing enzymes from the oxyhydrogen microorganisms belonging to the genus *Cupriavidus*;
wherein the chemosynthetic fixing reaction is at least partially driven by chemical and/or electrochemical energy provided by electron donors comprising gaseous $H_2$ and electron acceptors comprising gaseous $O_2$ that have been generated chemically and/or electrochemically and/or thermochemically and/or are introduced into the environment from at least one source external to the environment,
wherein gas phase mixtures of said gaseous $H_2$ and $O_2$, with the concentration of $H_2$ falling between 4% and 74.5%, are avoided within the bioreactor environment,
wherein $O_2$ gas is introduced into a first column within the environment by sparging, bubbling, and/or diffusion of said $O_2$ gas, and $H_2$ gas or syngas is introduced into a second column by sparging, bubbling, and/or diffusion of said $H_2$ gas or syngas, wherein there is a liquid connection between the first and second columns comprising the liquid culture medium, and wherein the liquid culture medium circulates between the first and second columns,
wherein the biomass and/or biochemicals are produced by the at least one chemosynthetic carbon-fixing reaction,
wherein the carbon-fixing reaction is maintained using a continuous influx and removal of nutrient medium and biomass, and wherein concentrations of the electron donors and the electron acceptors, and levels of nitrogen and phosphorous, are targeted at constant levels over time in a steady state, maintained at levels for maximum uptake and fixation of the inorganic carbon compound and/or the organic compound containing only one carbon atom and/or for maximum production of organic compounds comprising amino acids, peptides, and proteins,
wherein surplus biomass is removed from the bioreactor in order to maintain a constant population and cell density of said oxyhydrogen microorganisms in the liquid culture medium, and
wherein the biomass and/or biochemicals are separated from the environment and are processed into a product comprising an animal feed, a fertilizer, a soil additive, a soil stabilizer, a carbon source for large scale fermentations, and/or a nutrient source for the growth of other microbes or organisms.

2. The method according to claim 1, wherein said electron donors and/or organic compound containing only one carbon atom are generated through the gasification and/or pyrolysis of organic matter or through methane steam reforming and provided as a syngas to the oxyhydrogen microorganisms.

3. The method according to claim 2, wherein the ratio of hydrogen to carbon monoxide in the syngas is adjusted via the water gas shift reaction prior to delivery of the syngas to the oxyhydrogen microorganisms.

4. The method according to claim 1, wherein said thermochemical and/or electrochemical generation of electron donors and/or electron acceptors is powered by a carbon dioxide emission-free or low-carbon emission and/or a renewable source of power, and/or have been generated by gasification, pyrolysis, or steam reforming of a waste or biomass feedstock or biogas.

5. The method according to claim 4, wherein the carbon dioxide emission-free or low-carbon dioxide emission and/or renewable source of power is utilized for the electrochemical production of the electron donor.

6. The method according to claim 5, wherein the electrochemical production of the electron donor comprises electrolysis.

7. The method according to claim 1, wherein said electron donors and/or electron acceptors are generated or recycled using renewable, alternative, or conventional sources of power that are low in greenhouse gas emissions, wherein said source(s) of power is selected from at least one of: photovoltaics; solar thermal; wind power; hydroelectric; nuclear; geothermal; enhanced geothermal; ocean thermal; ocean wave power; and tidal power.

8. The method according to claim 1, wherein said thermochemical and/or electrochemical generation of electron donors and/or electron acceptors comprise one or more of the following: electrolysis of water by approaches including one or more of Proton Exchange Membranes (PEM), liquid electrolytes, high-pressure electrolysis, high temperature electrolysis of steam (HTES); thermochemical splitting of water through one or more of the iron oxide cycle, cerium (IV) oxide-cerium(III) oxide cycle, zinc zinc-oxide cycle, sulfur-iodine cycle, copper-chlorine cycle, calcium-bromine-iron cycle, hybrid sulfur cycle; electrolysis of hydrogen sulfide; thermochemical splitting of hydrogen sulfide; other electrochemical or thermochemical processes known to produce hydrogen with low—or no—carbon dioxide emissions; the Kvxrner-process and other processes generating a carbon-black product; carbon capture and sequestration enabled gasification or pyrolysis of biomass.

9. The method according to claim 1, wherein said electron donors are generated from pollutants or waste products selected from one or more of the following: process gas; tail gas; enhanced oil recovery vent gas; biogas; acid mine drainage; landfill leachate; landfill gas; geothermal gas; geothermal sludge or brine; metal contaminants; gangue; tailings; sulfides; disulfides; mercaptans selected from one or more of methyl and dimethyl mercaptan and ethyl mercaptan; carbonyl sulfide; carbon disulfide; alkanesulfonates; dialkyl sulfides; thiosulfate; thiofurans; thiocyanates; isothiocyanates; thioureas; thiols; thiophenols; thioethers; thiophene; dibenzothiophene; tetrathionate; dithionite; thionate; dialkyl disulfides; sulfones; sulfoxides; sulfolanes; sulfonic acid; dimethyl sulfoniopropionate; sulfonic esters; hydrogen sulfide; sulfate esters; organic sulfur; sulfur dioxide and all other sour gases.

10. The method according to claim 1, wherein the oxyhydrogen microorganisms comprise Cupriavidus necator DSM 531.

11. The method according to claim 1, wherein the inorganic carbon compound comprises carbon dioxide.

12. The method according to claim 11, wherein the carbon dioxide comprises carbon dioxide gas, either alone and/or dissolved in a mixture or solution further comprising carbonate ion and/or bicarbonate ion.

13. The method according to claim 1, wherein the inorganic carbon compound comprises carbon contained in a solid phase.

14. The method according to claim 1, wherein the organic compound containing only one carbon atom comprises carbon monoxide, methane, methanol, formate, and/or formic acid.

15. The method according to claim 1, wherein said electron donors further comprise one or more of: ammonia; ammonium; carbon monoxide; dithionate; elemental sulfur; hydrocarbons; metabisulfites; nitric oxide; nitrites; sulfates; thiosulfates; sulfides; sulfites; thionate; thionite; transition metals or their sulfides; oxides; chalcogenides; halides; hydroxides; oxyhydroxides; phosphates; sulfates; carbonates, in dissolved or solid phases; and conduction or valence band electrons in solid state electrode materials.

16. The method according to claim 1, wherein said electron acceptors further comprise one or more of the following: carbon dioxide; nitrites; nitrates; ferric iron or other transition metal ions; sulfates; or valence or conduction band holes in solid state electrode materials.

17. The method according to claim 1, wherein the converting step is preceded by one or more chemical preprocessing steps in which said electron donors and/or said electron acceptors are generated and/or refined from at least one input chemical and/or are recycled from chemicals produced during the chemosynthetic carbon-fixing reaction and/or chemicals derived from waste streams from other industrial, mining, agricultural, sewage or waste generating processes.

18. The method according to claim 1, wherein the converting step is followed by one or more process steps in which any unused nutrients and/or process water left after removal of oxyhydrogen cell mass and/or chemical co-products of chemosynthesis and/or waste products or contaminants of the process stream produced during the fixing step are recycled back into the environment to support further chemosynthesis.

19. The method according to claim 1, wherein the carbon fixing reaction is conducted under aerobic, microaerobic, or facultative conditions.

20. The method according to claim 1, wherein said biochemicals comprise an organic chemical product with a carbon chain length of C5 or greater.

21. The method according to claim 20, wherein the organic chemical product comprises carbon chain length between C5 and C30.

22. The method according to claim 1, wherein said at least one chemosynthetic reaction is performed by oxyhydrogen microorganisms that have been improved, optimized or engineered for the fixation of the inorganic carbon compound and/or the organic compound containing only one carbon atom and the production of organic compounds.

23. The method according to claim 1, wherein the bioreactor does not comprise transparent materials that expose the oxyhydrogen microorganisms and/or cell extracts containing enzymes from the oxyhydrogen microorganisms to light.

24. The method according to claim 1, wherein energy for carbon fixation is provided by an abiotic process.

25. The method according to claim 1, wherein a feed gas comprising 2% -12% $O_2$ is introduced into the first column in the environment.

26. The method according to claim 1, wherein said $O_2$ gas is delivered to said bioreactor at a concentration in the range of 2% to 6%.

27. The method according to claim 1, wherein a feed gas comprising said $H_2$ gas and/or syngas is introduced into the environment, wherein the bioreactor comprises a gas headspace, wherein said $H_2$ and/or syngas that is not utilized by the microorganisms in the chemosynthetic carbon-fixing reaction passes through the liquid culture medium and into the gas headspace and is recirculated by pumping the un-utilized gas out of the headspace, compressing it, and pumping it back into the liquid culture medium.

28. The method according to claim 1, wherein said recirculated $H_2$ and/or syngas is pumped back into the liquid culture medium at the bottom of the second column in said bioreactor.

29. The method according to claim 1, wherein said biomass comprises a dry biomass concentration of at least 4 g/l in steady state in said continuous microbial culture.

30. The method according to claim 1, wherein said $O_2$ gas in the culture medium comprises dissolved oxygen that is controlled and targeted at a constant level over time in a steady state.

31. The method according to claim 1, wherein the bioreactor comprises a gas headspace, and wherein oxygen concentration in the headspace is controlled and targeted at a constant level over time in a steady state.

32. The method according to claim 1, wherein the bioreactor comprises a gas headspace, and wherein hydrogen concentration in the headspace is controlled and targeted at a constant level over time in a steady state.

33. The method according to claim 1, wherein said $H_2$ gas is introduced into the second column in the environment by bubbling through the liquid culture medium and/or by diffusing through a membrane that contacts the liquid culture medium and that is impermeable to the liquid culture medium, and wherein said $O_2$ gas is pumped into the liquid culture medium using sparging equipment, a diffuser, a bubble aerator, and/or venturi equipment.

34. The method according to claim 1,
wherein the said liquid medium flows in the direction of the introduced $O_2$ gas and the liquid medium flows countercurrent to the direction of the introduced $H_2$ gas or syngas.

35. The method according to claim 1,
wherein the liquid medium flows countercurrent to the direction of the introduced $O_2$ gas and the liquid medium flows in the direction of the introduced $H_2$ gas or syngas.

36. The method according to claim 1,
wherein the $O_2$ gas is bubbled forcefully such that the first column acts as an airlift reactor and drives the circulation of the culture medium between the first and second columns.

37. The method according to claim 1,
wherein the circulation of the liquid medium is assisted by impellers, turbines, and/or pumps.

38. The method according to claim 1,
wherein the oxyhydrogen microorganisms freely circulate along with the liquid medium between the said first and second columns.

* * * * *